(12) United States Patent
Zhou et al.

(10) Patent No.: US 8,487,157 B2
(45) Date of Patent: Jul. 16, 2013

(54) TRANSGENIC RODENTS HAVING NGF BETA GENE MUTANTS AND ITS PREPARATION METHODS, THE PREPARATION METHODS OF THE CORRESPONDING MUTANT PROTEINS AND THE RESULTING MUTANT PROTEINS

(75) Inventors: Zhiwen Zhou, Beijing (CN); Hongshan Zhang, Beijing (CN); Hongbo Chen, Beijing (CN)

(73) Assignee: Staidson (Beijing) Pharmaceutical Co., Ltd., Beijing (CN)

( * ) Notice: Subject to any disclaimer, the term of this patent is extended or adjusted under 35 U.S.C. 154(b) by 100 days.

(21) Appl. No.: 12/812,731

(22) PCT Filed: Mar. 7, 2008

(86) PCT No.: PCT/CN2008/070438
§ 371 (c)(1),
(2), (4) Date: Dec. 3, 2010

(87) PCT Pub. No.: WO2008/106896
PCT Pub. Date: Sep. 12, 2008

(65) Prior Publication Data
US 2011/0082285 A1 Apr. 7, 2011

(30) Foreign Application Priority Data
Mar. 7, 2007 (CN) .......................... 2007 1 0086017

(51) Int. Cl.
*A01K 67/027* (2006.01)
*A01K 67/033* (2006.01)

(52) U.S. Cl.
USPC .................................. 800/18; 800/4; 800/25

(58) Field of Classification Search
USPC ................................................. 800/18, 4, 25
See application file for complete search history.

(56) References Cited

U.S. PATENT DOCUMENTS

| 5,489,743 A | 2/1996 | Robinson et al. |
| 5,602,307 A | 2/1997 | Beaudet et al. |
| 5,986,070 A | 11/1999 | Collins et al. |

FOREIGN PATENT DOCUMENTS

| CN | 1051934 A | 6/1991 |
| CN | 1079992 A | 12/1993 |
| CN | 1271736 A | 11/2000 |
| CN | 1793375 A | 6/2006 |
| WO | 2005/040335 A2 | 5/2005 |

OTHER PUBLICATIONS

Taft et al, Trends in Genetics 22(12):649-653, 2006.*
Linder, Lab. Anim. 30(5):34-39, 2001.*
Bilbo et al, Lab. Anim. 30(1):24-29, 2001.*
Holschneider et al, Int. J. Dev. Neuroscience 18 :615-618, 2000.*
Wood. Comp. Med. 50(1): 12-15, 2000.*
Sigmund, Arterioscler. Throm. Vasc. Biol. 20:1425-1429, 2000.*
Kappel et al. Current Opinion in Biotechnology 3:548-553, 1992.*
Ullrich et al. (1983) Nature, vol. 303, 821-825.*
van der Weyden et al. (2002) Physiol. Genomics, vol. 11, 133-164.*
International Search Report and Written Opinion of PCT/CN2008/070438 dated Jun. 12, 2008.
Extended European Search Report issued in corresponding EP Application No. 08715174.2 on Aug. 6, 2010 (in the name of Staidson (Beijin) Pharmaceutical Co., Ltd.).
Office Action issued in corresponding EP Application No. 08715174.2 on Mar. 30, 2011 (in the name of Staidson (Beijing) Pharmaceutical Co., Ltd.).
Office Action issued in corresponding CN Application No. 200710086017.3 on Dec. 24, 2010.
Anna M. Colangelo et al., "Recombinant human nerve growth factor with a marked activity in vitro and in vivo", PNAS, 2005, 102(51): 18658-18663.
Craig Crowley et al., "Mice Lacking Nerve Growth Factor Display Perinatal Loss of Sensory and Sympathetic Neurons yet Develop Basal Forebrain Cholinergic Neurons", Cell, 1994, 76: 1001-1011.
S. Coulibaly et al., "Human nerve growth factor beta (hNGF-Beta): mammary gland specific expression and production in transgenic rabbits", FEBS Letters, 1999, 444: 111-116.
Alborz Hassankhani et al., "Overexpression of NGF within the Heart of Transgenic Mice Causes Hyperinnervation, Cardiac Enlargement, and Hyperplasia of Ectopic Cells", Developmental Biology, 1995, 169: 309-321.
Gary W. Hoyle et al., "Hyperinnervation of the Airways in Transgenic Mice Overexpressing Nerve Growth Factor", Am. J. Respir. Cell Mol. Biol., 1998, 18: 149-157.

* cited by examiner

Primary Examiner — Anne Marie S Wehbe
(74) Attorney, Agent, or Firm — Sughrue Mion, PLLC

(57) ABSTRACT

Transgenic rodents having NGF beta gene mutants in their genomes express NGF beta mutant proteins. The preparation methods of the transgenic rodents, the methods of utilizing the transgenic animals to prepare NGF beta mutant proteins and the resulting NGF beta mutant proteins are provided. The transgenic rodents are useful in preparing human NGF and in the study of the functions of NGF beta mutants and their receptors in the whole animal level, and also useful for screening and purifying NGF beta mutants which have high activity and high security.

5 Claims, 15 Drawing Sheets

```
                        SEQUENCE LISTING

<160> NUMBER OF SEQ ID NOS: 26

<210> SEQ ID NO 1
<211> LENGTH: 33
<212> TYPE: DNA
<213> ORGANISM: Artificial Sequence
<220> FEATURE:
<223> OTHER INFORMATION: Synthetic oligonucleotide primer sequence

<400> SEQUENCE: 1
cggaattcgt ccctagctca cttcattcaa gga                                 33

<210> SEQ ID NO 2
<211> LENGTH: 40
<212> TYPE: DNA
<213> ORGANISM: Artificial Sequence
<220> FEATURE:
<223> OTHER INFORMATION: Synthetic oligonucleotide primer sequence

<400> SEQUENCE: 2
ggaagatggg atgggaggat gagcgcttgc tccggtgagt                          40

<210> SEQ ID NO 3
<211> LENGTH: 50
<212> TYPE: DNA
<213> ORGANISM: Artificial Sequence
<220> FEATURE:
<223> OTHER INFORMATION: Synthetic oligonucleotide primer sequence

<400> SEQUENCE: 3
actcaccgga gcaagcgctc atcctcccat cccatcttcc acagggcga               50

<210> SEQ ID NO 4
<211> LENGTH: 35
<212> TYPE: DNA
<213> ORGANISM: Artificial Sequence
<220> FEATURE:
<223> OTHER INFORMATION: Synthetic oligonucleotide primer sequence
```

```
<400> SEQUENCE: 4
gggctgcagg caagtcaggc tcttctcaca gcctt                              35

<210> SEQ ID NO 5
<211> LENGTH: 47
<212> TYPE: DNA
<213> ORGANISM: Artificial Sequence
<220> FEATURE:
<223> OTHER INFORMATION: Synthetic oligonucleotide primer sequence

<400> SEQUENCE: 5
aaggctgtga gaagagcctg acttgcctgc agcccccttc cccacct                 47

<210> SEQ ID NO 6
<211> LENGTH: 30
<212> TYPE: DNA
<213> ORGANISM: Artificial Sequence
<220> FEATURE:
<223> OTHER INFORMATION: Synthetic oligonucleotide primer sequence

<400> SEQUENCE: 6
accagatctg ccatgacagg cctcaggaga                                    30

<210> SEQ ID NO 7
<211> LENGTH: 41
<212> TYPE: DNA
<213> ORGANISM: Artificial Sequence
<220> FEATURE:
<223> OTHER INFORMATION: Synthetic oligonucleotide primer sequence

<400> SEQUENCE: 7
cggaattcgt cgacggtttc atgttaagat tgcctttgct c                       41

<210> SEQ ID NO 8
<211> LENGTH: 46
<212> TYPE: DNA
<213> ORGANISM: Artificial Sequence
<220> FEATURE:
<223> OTHER INFORMATION: Synthetic oligonucleotide primer sequence

<400> SEQUENCE: 8
cggaattcgc ggccgctcct ggaaccagga gtcagaggga atggat                  46

<210> SEQ ID NO 9
<211> LENGTH: 40
<212> TYPE: DNA
<213> ORGANISM: Artificial Sequence
<220> FEATURE:
<223> OTHER INFORMATION: Synthetic oligonucleotide primer sequence

<400> SEQUENCE: 9
ggaagactgg gtgggtggat gagcgcttgc tccggtgagt                         40

<210> SEQ ID NO 10
<211> LENGTH: 49
<212> TYPE: DNA
<213> ORGANISM: Artificial Sequence
<220> FEATURE:
<223> OTHER INFORMATION: Synthetic oligonucleotide primer sequence

<400> SEQUENCE: 10
actcaccgga gcaagcgctc atccacccac ccagtcttcc acatggggg               49

<210> SEQ ID NO 11
<211> LENGTH: 35
```

```
<212> TYPE: DNA
<213> ORGANISM: Artificial Sequence
<220> FEATURE:
<223> OTHER INFORMATION: Synthetic oligonucleotide primer sequence

<400> SEQUENCE: 11
gggctgcagg caagtcagcc tcttcttgta gcctt                              35

<210> SEQ ID NO 12
<211> LENGTH: 47
<212> TYPE: DNA
<213> ORGANISM: Artificial Sequence
<220> FEATURE:
<223> OTHER INFORMATION: Synthetic oligonucleotide primer sequence

<400> SEQUENCE: 12
aaggctacaa gaagaggctg acttgcctgc agcccccttc cccacct                 47

<210> SEQ ID NO 13
<211> LENGTH: 27
<212> TYPE: DNA
<213> ORGANISM: Artificial Sequence
<220> FEATURE:
<223> OTHER INFORMATION: Synthetic oligonucleotide primer sequence

<400> SEQUENCE: 13
gctcatcctc ccatcccatc ttccaca                                       27

<210> SEQ ID NO 14
<211> LENGTH: 26
<212> TYPE: DNA
<213> ORGANISM: Artificial Sequence
<220> FEATURE:
<223> OTHER INFORMATION: Synthetic oligonucleotide primer sequence

<400> SEQUENCE: 14
gaacgagatc agcagcctct gttcca                                        26

<210> SEQ ID NO 15
<211> LENGTH: 27
<212> TYPE: DNA
<213> ORGANISM: Artificial Sequence
<220> FEATURE:
<223> OTHER INFORMATION: Synthetic oligonucleotide primer sequence

<400> SEQUENCE: 15
gctcatccac ccacccagtc ttccaca                                       27

<210> SEQ ID NO 16
<211> LENGTH: 26
<212> TYPE: DNA
<213> ORGANISM: Artificial Sequence
<220> FEATURE:
<223> OTHER INFORMATION: Synthetic oligonucleotide primer sequence

<400> SEQUENCE: 16
gaacgagatc agcagcctct gttcca                                        26

<210> SEQ ID NO 17
<211> LENGTH: 27
<212> TYPE: DNA
<213> ORGANISM: Artificial Sequence
<220> FEATURE:
<223> OTHER INFORMATION: Synthetic oligonucleotide primer sequence

<400> SEQUENCE: 17
acaggactca ccggagcaag cgctcat                                       27
```

<210> SEQ ID NO 18
<211> LENGTH: 26
<212> TYPE: DNA
<213> ORGANISM: Artificial Sequence
<220> FEATURE:
<223> OTHER INFORMATION: Synthetic oligonucleotide primer sequence

<400> SEQUENCE: 18
gaacgagatc agcagcctct gttcca                                      26

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide primer sequence

<400> SEQUENCE: 19
gaactcccag tgtggataag taga                                        24

<210> SEQ ID NO 20
<211> LENGTH: 27
<212> TYPE: DNA
<213> ORGANISM: Artificial Sequence
<220> FEATURE:
<223> OTHER INFORMATION: Synthetic oligonucleotide primer sequence

<400> SEQUENCE: 20
aatagtagag aagcagccat cagagca                                     27

<210> SEQ ID NO 21
<211> LENGTH: 30
<212> TYPE: DNA
<213> ORGANISM: Artificial Sequence
<220> FEATURE:
<223> OTHER INFORMATION: Synthetic oligonucleotide primer sequence

<400> SEQUENCE: 21 aatcccttc aacaggactc accggagcaa                                   30

<210> SEQ ID NO 22
<211> LENGTH: 29
<212> TYPE: DNA
<213> ORGANISM: Artificial Sequence
<220> FEATURE:
<223> OTHER INFORMATION: Synthetic oligonucleotide primer sequence

<400> SEQUENCE: 22 aaggggggctg caggcaagtc agcctcttc                                  29

<210> SEQ ID NO 23
<211> LENGTH: 363
<212> TYPE: DNA
<213> ORGANISM: Homo sapiens

<400> SEQUENCE: 23
tcatcatccc atcccatctt ccacaggggc gaattctcgg tgtgtgacag tgtcagcgtg    60
tgggttgggg ataagaccac cgccacagac atcaagggca aggaggtgat ggtgttggga   120
gaggtgaaca ttaacaacag tgtattcaaa cagtactttt ttgagaccaa gtgccgggac   180
ccaaatcccg ttgacagcgg gtgccgggc attgactcaa agcactggaa ctcatattgt   240
accacgactc acacctttgt caaggcgctg accatggatg gcaagcaggc tgcctggcgg   300
tttatccgga tagatacggc ctgtgtgtgt gtgctcagca ggaaggctgt gagaagagcc   360

```
tga                                                                    363

<210> SEQ ID NO 24
<211> LENGTH: 30
<212> TYPE: DNA
<213> ORGANISM: Artificial Sequence
<220> FEATURE:
<223> OTHER INFORMATION: Synthetic oligonucleotide primer sequence

<400> SEQUENCE: 24 aatcccttc aacaggactc accggagcaa                                         30

<210> SEQ ID NO 25
<211> LENGTH: 29
<212> TYPE: DNA
<213> ORGANISM: Artificial Sequence
<220> FEATURE:
<223> OTHER INFORMATION: Synthetic oligonucleotide primer sequence

<400> SEQUENCE: 25 aaggggctg caggcaagtc agcctcttc                                          29

<210> SEQ ID NO 26
<211> LENGTH: 363
<212> TYPE: DNA
<213> ORGANISM: Mus musculus

<400> SEQUENCE: 26
tcatccaccc acccagtctt ccacatgggg gagttctcag tgtgtgacag tgtcagtgtg        60
tgggttggag ataagaccac agccacagac atcgccggcg cggctgtgac agtgctggcc      120
gaggtgaaca ttaacaacag tgtattcaga cagtactttt ttgagaccaa gtgccgagcc      180
tccaatcctg ttgagagtgg gtgccggggc atcgactcca aacactggaa ctcatactgc      240
accacgactc acaccttcgt caaggcgttg acaacagatg agaagcaggc tgcctggagg      300
ttcatccgga tagacacagc ctgtgtgtgt gtgctcagca ggaaggctac aagaagaggc      360
tga                                                                    363
```

TRANSGENIC RODENTS HAVING NGF BETA GENE MUTANTS AND ITS PREPARATION METHODS, THE PREPARATION METHODS OF THE CORRESPONDING MUTANT PROTEINS AND THE RESULTING MUTANT PROTEINS

FIELD OF THE INVENTION

The present invention relates to a transgenic animal, the obtaining method thereof, the method of using this transgenic animal to prepare the corresponding gene expression product, and the gene expression product using this method. Particularly, the present invention relates to a transgenic rodent stably expressing the target gene; and to the method for obtaining the transgenic rodent stably expressing the target gene using the embryonic stem cell (ES) culture technology and homology recombination technology to integrate the target gene into the genome and substitute the corresponding gene of the rodent; and to the method of preparing the corresponding protein of target gene using the transgenic rodent expressing the target gene stably, and the protein obtained by the method. More particularly, the present invention relates to the method of preparing the corresponding mutein of mutant NGF-β gene, and the protein obtained by this method.

BACKGROUND

NGF (Nerve Growth Factor) was the first regulator of neuron growth to be discovered and confirmed, and the best described neurotrophic factor. [Ho J L, He S, Hu A et al., J Exp Med, 1995, 181 (4):1493-1505]. NGF plays important roles in the stages of the proliferation and phenotypic differentiation of neural stem cells, the development of neurons, the growth of axons, the synthesis of neurotransmitters and cells' apoptosis, etc. [Sayada C, Denamur E, Elion J et al., Gene, 1992, 120 (1):129-130]. NGF regulates the differentiation and maturation of sympathetic and sensory neurons, is involved in supporting the normal function of the adult sympathetic neuron, and nutritionally supports the adult sensory neurons [Zhang D, Yang X, Berry J, et al., J In2fect Dis, 1997, 176 (4): 1035-1040]. The developments and differentiations of cholinergic neurons of basal forebrain and the cholinergic interneurons of striatum in the central nervous system are also regulated by NGF [Pal S, Barnhart K M, Wei Q, et al., Vaccine, 1999, 17 (5):459-465]. Because of the importance of NGF's physiologic activity, it is demonstrated that NGF is of very important clinical application values.

Human NGF consists of three types of peptide chains: α, β and γ, which are bound together by non-covalent bonds in the form of $\alpha_2\beta_2\gamma_2$. It is further demonstrated that the β subunit possesses the whole bioactivity of the NGF, wherein the β subunit is a dimmer consisting of two 118-amino-acid chains bonded by non-covalent bonds. There are three disulfide bonds in each monomer; and the correct formation of the three disulfide bonds (Cys58-Cys108, Cys68-Cys110, Cys15-Cys80) is the critical base for the protein folding, and then affects the bioactivity of NGF-β. Because of the vanishing concentration and content of human NGF-β in the adult human body and the unavailability of human tissue, it cannot be produced in large quantities via extraction from human tissues. And, the NGF-β preparation produced from the general bacteria (For example, E. coli) and yeast expression systems via recombinant technologies exhibits less bioactivity than the NGF-β extracted from animal organs. This is because there are not natural modification and dimerization in the these two systems [De Bernardez Clark E, Schwarz E, Rudolph, R et al., 1999; 309:217-36. Ikemura H, Takagi H, Inouye M, et al., J Biol Chem. 1987 Jun. 5; 262(16):7859-64. Nishizawa M, Ozawa F, Higashizaki T, et al., Appl. Microbiol Biotechnol. 1993 February; 38(5):624-30.]. Theoretically, there would be greater advantage to use mammal cells to express and prepare human NGF-β; however their low expression level and high cost tend to hamper large-scale production. [C. ANTHONY ALTAR, Louis E. BURTONt, GREGORY L. Proc. Natl. Acad. Sci. USA Vol. 88, pp. 281-285, January 1991)]. Moreover, the bioactivity of human NGF-β prepared by the non-human mammal cell system is incomparable to the NGF extracted from humans. One clinical trial based on the recombinant human NGF for diabetic neuropathy developed by Genentech, Inc. failed in Phase III because of poor therapeutic effect [Apfel SC. Int. Rev. Neurobiol 50: 393-413, 2002]. As of this writing, no recombinant human NGF has been approved as drugs on the market, though various strategies and efforts have been continually proposed based on recombinant technology in different expression systems such as bacteria, yeasts, CHO cells and insect cells.

The content of NGF in the submandibular gland is higher than in all remaining tissues or organs of adult male mouse. Moreover, mice propagate rapidly and are easy to be bred in large scale with compliance to industrial requirement. Thus, mice are supposed to be an ideal source for extracting and purifying NGF. The NGF-β with best biological activity and unlimited source on the market is extracted from mice submandibular gland. However, compared with human NGF, the therapeutic efficacy of mouse NGF on rodent experimental model of allergic myeloencephalitis and Parkinson's disease is not as good as that of human NGF. Furthermore, mouse NGF is more immunogenic to human than human nerve growth factor theoretically. And the stability and safety of human NGF maybe better than that of mouse NGF when applied in human.

There are a number of human genes are homologous to the mouse's, and the mouse is easy to feed because of the smaller size and relative shorter life cycle, thus mouse is one of the best model animal to investigate the gene function of mammal animals and human diseases. During the past several years, many kinds of mice have been genetic engineered to express heterogenous proteins through the gene targeting technology. The biological function of NGF and the interaction of NGF with its receptor are always attracting a lot interest in the field of neurobiology and developmental biology. Crowley et al used knock-out technology to destroy the mouse NGF gene, and investigated the influence of NGF on the development of neurons (Crowley C, Spencer S D, Nishimura M C, et. al, Cell. 1994 Mar. 25; 76(6):1001-11). It is demonstrated that the development and survival of sympathetic and sensory neuron depend strictly on NGF, and that this dependence cannot be compensated by other neurotrophins. Moreover, Smeyne et al. knocked out the cellular high-affinity receptor TrkA of NGF to investigate the function of TrkA in the development of neurons (Smeyne R J, Klein R, Schnapp A, et al. Nature. 1994 Mar. 17; 368(6468):193-4.). However, if all of the NGF gene or its receptor TrkA genes are knocked out, then the mouse will either die during its early embryonic development or be born with low vitality because of the depletion of NGF's physiological activity. This may be also one of the reason why there is no research to apply the knock-out strategy to study the specific interaction between NGF and its receptor. The mutant NGF obtained in vitro provides a good basis to investigate the interaction between NGF and its receptor. For example, the mutant NGF which binds the TrkA only (rather than the low affinity receptor P75)

may be used to investigate the function of P75, which make the investigation more targeted, pertinent and specific (Horton A, Laramee G, Wyatt S, et al., Mol Cell Neurosci. 1997; 10(3-4):162-72. Ryden M, Hempstead B, Ibanez C F, et al., J Biol Chem. 1997 Jun. 27; 272(26):16322-8). But the in vitro gene mutant cannot reveal the effect of mutations during the individual development in the complex in vivo condition. Thus, it remains to be elucidated how to modify the NGF gene of animal to stably express mutein of NGF of said animal and study the function of NGF mutant and its receptor in the level of whole animal.

SUMMARY OF THE INVENTION

The object of the present invention is to solve the above problems of the prior art: the expression of human NGF-β and the mutation thereof using mammal cells produces little and is difficult perform in large scale; the mouse NGF is of poor therapeutic effect and of possible great immunogenicity; and there are some limitations associated with the gene knock-out method to investigate the specific interactions between NGF and the receptor thereof.

The present invention provides a transgenic rodent animal, wherein the genome of said animal comprises a mutant of NGF-β gene, and said animal expresses the mutein of NGF-β.

The term "mutein of NGF-β" used in present invention refers to a mutein possessing the activity of NGF-β protein, and its homology to the wild NGF-β protein of rodent animals is at least 70%, preferably at least 80%, more preferably at least 90%. For example, a mutein of NGF-β may be the protein comprising the amino acid sequence of human NGF-β protein or the mutein thereof. That is, the transgenic rodents of the present invention preferably express a human NGF-β protein or the mutein thereof.

In the present invention, the homology between amino acid sequences may be typically determined by using existing software or computer programs such as the BestFit or Gap matching programs.

In the present invention, the mutant of NGF-β gene presents in at least one chromosome of the transgenic rodent's genome. Preferably, all the NGF-β genes in said genomes of said transgenic rodent are the mutants of NGF-β gene. And preferably, said mutant of NGF-β gene is a human NGF-β gene or its mutant. Preferably, the transgenic rodent is a transgenic mouse.

The present invention also provides a method for obtaining a transgenic rodent, characterized in changing the NGF-β gene of a rodent by a homologous recombination technique, such that the obtained transgenic rodent comprises the mutant of NGF-β gene in it genome, and expresses the mutein of NGF-β. Wherein, said transgenic rodent preferably expresses a human NGF-β protein or the mutein thereof.

The present method for obtaining the transgenic rodent preferably comprises the steps as follows:

1) Constructing a targeting vector, wherein said vector comprises the target gene, i.e. the mutant of NGF-β gene;
2) Using the targeting vector obtained in step 1) to transfect the embryonic stem cells;
3) Preparing a donor blastocyst;
4) Microinjecting the transfected embryonic stem cells obtained in step 2) into the donor blastocyst obtained in step 3);
5) Transferring the donor blastocyst obtained in step 4) to a uterus of a acceptor; and
6) Obtaining the transgenic animal.

When constructing the targeting vector, the length of the homologous arm has great influence on the targeting efficiency. Generally, the longer the homologous arm, the higher frequency of homologous recombination. Thus, the length of most homologous arms is between 5 kb and 8 kb. The relative positions of the homologous arms and positive-negative selection markers decide that only the successfully targeted clones through homologous recombination may be screened out by the corresponding medicine selective media. Generally, PCR is used to further confirm whether the targeting is successful or not. The principle of designing primers is that: one primer anneals with the positive selection marker sequence, and another anneals with the sequence of the genome adjacent to the lateral side of the targeting vector. The amplification efficiency depends on the distance between the two primers; thus, commonly, the lengths of both homologous arms are dissymmetric. The length difference between long arms and short arms will be convenient for the measurement by PCR. Meanwhile, the long arms should be long enough, to ensure enough homologous sequence to form the exchange complex of chromosome. In order to increase the frequency of homologous recombination and avoid the difficulty in the experimental operation and complexity in the following measurement caused by the too-long arms, the length of the short arm preferably is 1 to 10 kb, more preferably 2 kb. The length of long arm preferably is 1 to 10 kb, more preferably 3-8 kb, most preferably 5 kb.

As is well known in the field, regarding vector selection, "vector" is the means to enable or assist carrying the entity from one environment to another. Some vectors used in recombination DNA technology may carry the DNA fragment (such as the heterogenous cDNA fragment) into the host and/or the target cells, achieving the object of duplicating the vector, which comprises the nucleotide sequences used in the present invention and/or the nucleotide sequences expressing the protein used in the present invention. Examples of vectors used in the recombination DNA technology include, but are not limited to, plasmid, chromosome, artificial chromosome and virus. The vectors used in the present invention include, but are not limited to, the plasmid vectors such as pLoxPneo, pPNT, etc.

The present invention also relates to the method of preparing the NGF-β mutein by using the transgenic rodent of the present invention, comprising the steps as follows:

1) Feeding a transgenic rodent(s) of the present invention;
2) Extracting target protein from the tissue of the rodent(s) fed in step 1).

Wherein said target protein possesses the activity of nerve growth factor (NGF). In case of said transgenic rodents express human NGF-β protein or the mutein thereof, the extracted target protein is human NGF-β protein or the mutein thereof. The rodent is preferably a mouse.

There is no special limitation regarding which animal tissue the target protein may be extracted from; tissues that may undergo extractions include, but are not limited to, submandibular glands.

The mutein of NGF-β prepared by using the above methods of the present invention refers to a mutein possessing the activity of NGF-β protein with a homology to the wild-type NGF-β protein of rodents of at least 70%, preferably at least 80%, more preferably at least 90%. For example, it may be the protein having the amino acid sequence of a human NGF-β protein or that of its mutein. That is, preferably, the transgenic rodent of the present invention expresses a human NGF-β protein or a mutein thereof.

Further, the present invention also provides the mutein of the rodent's NGF-β protein, which is obtained by the method of preparing the mutein of NGF-β protein according to the present invention, wherein, the rodent is preferably a mouse.

In the present invention, the mutein of mouse NGF-β protein refers to the mutein possessing the activity of NGF-β protein, and its homology to the mouse NGF-β protein is at least 70%, preferably at least 80%, more preferably at least 90%. For example, it may be the protein comprising the amino acid sequence of a human NGF-β protein or that of its mutein.

A mutein of NGF-β prepared by the method of preparing the NGF-β mutein according to the present invention may be formulated into a pharmaceutically acceptable pharmaceutical composition. In the present invention, "pharmaceutical composition" refers to a composition comprising or consisting of a therapeutically effective amount of pharmaceutically active agent. Preferably, a pharmaceutical composition of the present invention may comprise a pharmaceutically acceptable carrier, diluent or excipient, or the combination thereof. A pharmaceutically acceptable carrier or diluent may be those well known in the filed of pharmacy. The selection of a pharmaceutical carrier, excipient or diluent may be performed according to desired administration routes and standard pharmacy practices. Such pharmaceutical compositions may comprises (or additionally comprises) an excipient, a diluent, any proper binder, lubricant, suspending agent, coating agent and solvent. Examples of pharmaceutically acceptable carrier include water, salt solution, ethanol, silicone resin, wax, vaseline oil, petroleum jelly, vegetable oil, polyethylene glycol, propanediol, liposome, sugar, gel, lactose, starch sugar, magnesium stearate, mica, surfactant, silicic acid, viscous paraffin, perfume essential oil, monoglyceride and diglyceride, petroleum hydrocarbon fatty acid ester, hydroxyl methylcellulose, polyvinylpyrrolidone, mannitol, amino acid, etc. Such proteins are preferably formulated into the dosage form of injection or eye drops.

The present invention uses knock-in technology to provide a new way of producing human NGF. The NGF-β gene of a rodent is replaced with the human NGF-β gene by using the techniques of homologous recombination and the culturing ES of a rodent (e.g., a mouse), after which ample matured human NGF-β protein may be extracted from the submandibular glands of the transgenic rodent, thus it can be used to investigate and produce such proteins in a large scale.

The present invention uses gene knock-in technique to construct the mutant NGF-β within the rodent, and obtains the rodent animal with NGF-β mutant (such as mouse with NGF-β mutant). Because the negative influence upon the animal that experiences a knock-in is much less than that upon the animal that experiences the existing gene knock-out technique, the present invention also provides a new way to investigate the function of NGF-β mutant and its receptor at the level of the whole animal. What's more, the invention also provides a new way to screen and purify in vivo safe and highly active NGF-β mutant.

When compared with the existing technology to express human NGF-β protein using mammal cells, the advantages of the present invention are as follows:

First, the human NGF-β protein obtained by using mammal cells in the cellular level is the product of in vitro culture condition. This is because all kinds of complex in vivo environments that occur during an animal's growth and development cannot be completely repeated (such as the changing of hormone, the interaction of α subunit with γ subunit, the quaternary structure formation of β subunit dimmers). Thus the yield of human NGF-β protein is low, and the difference between such human NGF-β protein and the natural human NGF-β protein is great. Because the present invention produces the human NGF-β proteins at the whole-animal level after undergoing the entire growth and development process, using this method is closest to the natural way, thus the difference between such human NGF-β proteins and with the natural ones is small, thereby said human NGF-β proteins are of high activity.

Second, mammal cells trend to mutate during the culturing, which causes degeneration leading to unstable and discontinuous production of human NGF-β protein. In contrast, the mutation frequency of a present transgenic rodent during the course of feedings and proliferation is much lower than that of mammal cells cultured in vitro. The progeny of heterozygous and homozygous transgenic rodents will be able to produce human NGF-β protein stably, as long as they carry the gene being transferred into.

Third, while culturing mammal cells involve comparatively high costs, strict conditions, and low yields, the present transgenic rodent is easily fed and rapidly bred, enabling human NGF-β protein to be extracted amply and economically.

The technical solution can be applied not only to a rodent, but also to the animal comprising NGF-β gene in genome, including, but not limited to, rodents, pigs, cats, humans, chickens, snakes, frogs, fishes, etc. Rodents including, but not limited to, mice, rats, etc., are the preferred. Mice are the most preferred.

DETAILED DESCRIPTION OF THE INVENTION

Example 1

Figure 1A:
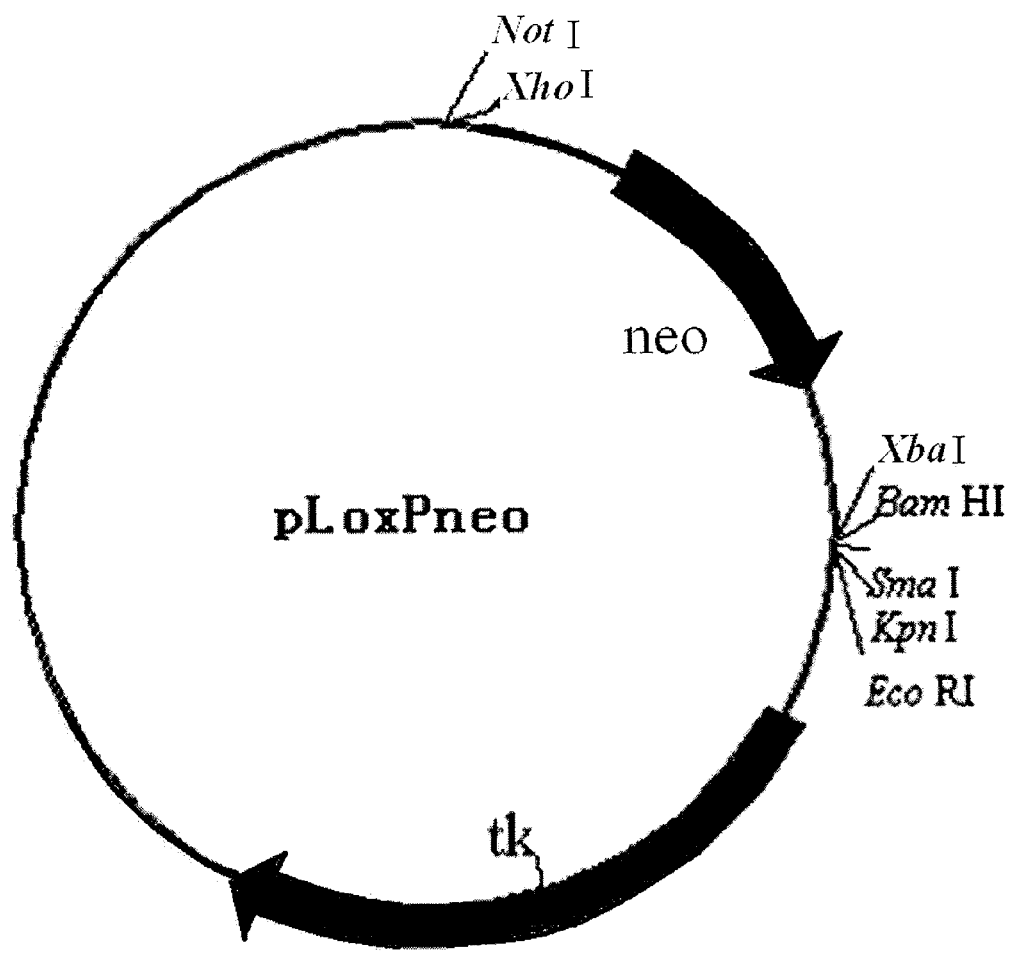
FIG. 1A is the schematic diagram showing the structure of pLoxPneo vector plasmid.

Construction of a Targeting Vector of Mature Human NGF Peptide

1) The Following Primers were Synthesized:

P1
(SEQ ID No. 1)
Eco RI
CGGAATTCgtccctagctcacttcattcaagga

P2
(SEQ ID No. 2)
ggaagatgggatgggaggatgagcgcttgctccggtgagt

P3
(SEQ ID No. 3)
actcaccggagcaagcgctcatcctcccatcccatcttccacaggggcga

P4
(SEQ ID No. 4)
gggctgcaggcaagtcaggctcttctcacagcctt

P5
(SEQ ID No. 5)
aaggctgtgagaagagcctgacttgcctgcagccccttccccacct

P6
(SEQ ID No. 6)
Bgl II
ACCAGATCTgccatgacaggcctcaggaga

P7
(SEQ ID No. 7)
Sal I
CGGAATTCGTCGACggtttcatgttaagattgcctttgctc

P8
(SEQ ID No. 8)
Not I
CGGAATTCGCGGCCGCtcctggaaccaggagtcagagggaatggat

2) Construction of an Upstream Long Arm:

By using mouse genomic DNA (1 μg) as template, P1+P2 as primers (100 ng each), Pfu high fidelity polymerase (2.5 U), 250 μmol/L dNTPs, 2.5 mmol/L MgCl2 and 25 mmol/L Tris HCl (pH8.3), a PCR reaction (94° C. 30 s, 55° C. 30 s, 72° C. 4 min, 30 cycles, Perkin Elmer 9700 PCR Amplifier) was performed. A Qiagen Gel Extraction Kit (from QIAGEN) and electrophoresis in 1% agarose was used. The PCR product was purified, and then obtained DNA fragments of about 4.4 kb. The PCR amplification reaction (under the same conditions as the above, except the extension time at 72° C. was 45 s) was performed by using human genomic DNA (1 μg) as template and P3+P4 as primers (100 ng each) to obtain the amplified DNA fragments of 0.37 kb. Then the isolation and purification were performed by using the same electrophoresis as above. The PCR amplification (under the same condition as above) is performed by using mouse genomic DNA as template and P5+P6 as primers (100 ng each). Then DNA fragments of 0.65 kb were purified and obtained, and then the isolation and purification were performed by using the same electrophoresis as above. The above three kinds of DNA product fragments (100 ng each) were mixed as PCR template, the PCR amplification reaction was performed (under the same condition as above, excepting the extension time at 72° C. was 5 minutes) by using P1+P6 as primers (100 ng each) obtaining DNA fragments of 5.4 kb, and then the isolation and purification were performed by using the same electrophoresis as above.

3) Construction of a Downstream Short Arm:

PCR amplification reaction (under the same condition as above, except the extension time at 72° C. is 2 min) was performed with mouse genomic DNA (1 μg) as template and P7+P8 (100 ng each) as primers obtaining DNA fragments of 2 kb, and then the isolation and purification were performed by using the same agarose electrophoresis as above.

Figure 1B:
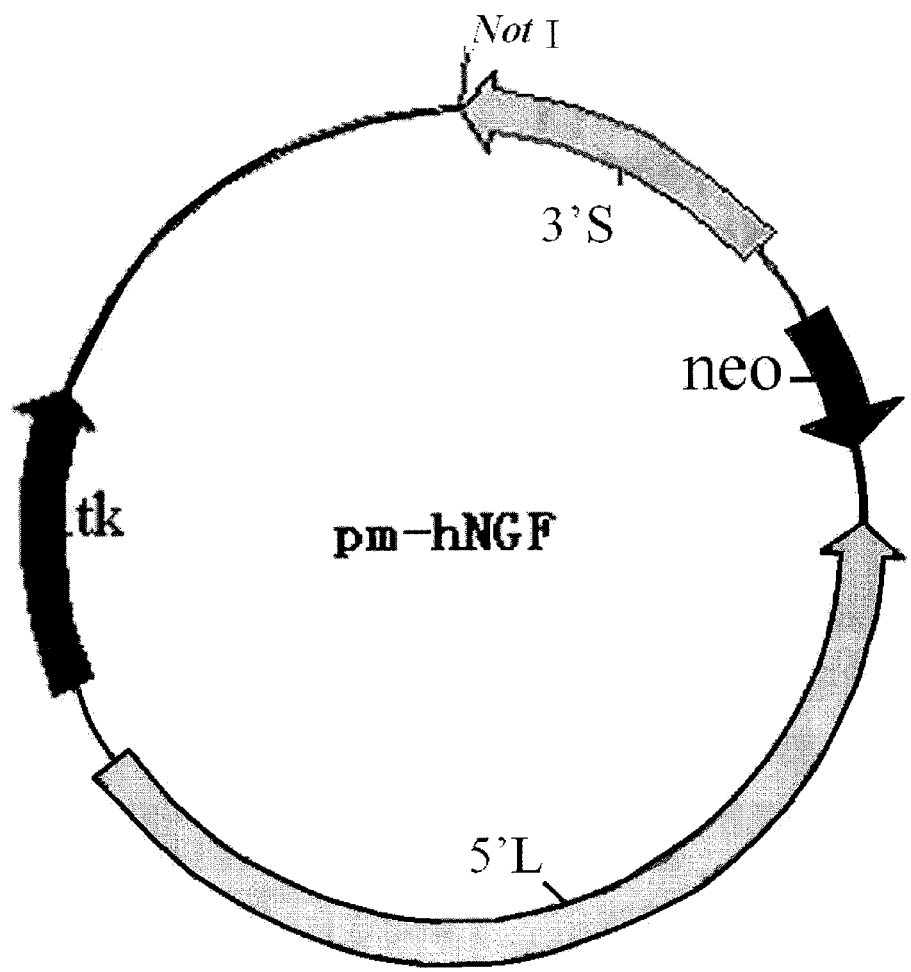
FIG. 1B is the schematic diagram showing the structure of targeting vector pm-hNGF.
Figure 1C:
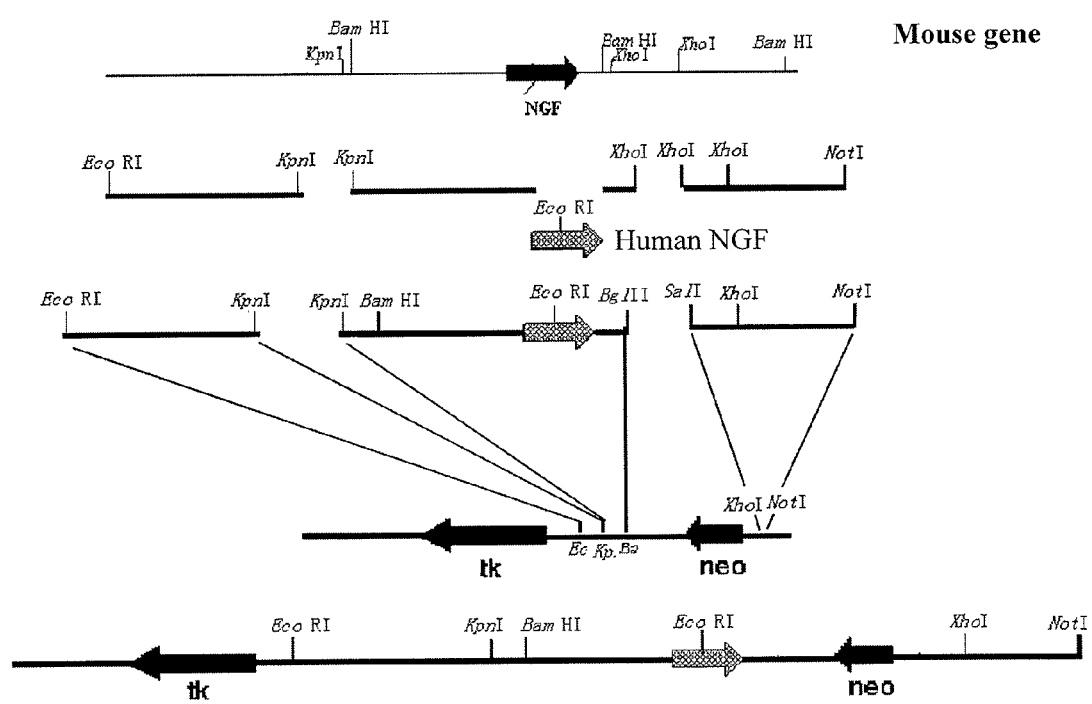
FIG. 1C is the schematic diagram showing the process of constructing the targeting vector pm-hNGF.

4) Construction of a Targeting Vector:

The pLoxPneo vector (FIG. 1A) with Eco RI+Kpn I (Biolabs, hereinafter using the same) was digested and purified with a Qiagen Gel Extraction Kit after the electrophoresis in 1% agarose. The upstream long arm DNA fragment with Eco RI+Kpn I was digested and purified the 2.06 kb DNA fragment after the same electrophoresis as above (middle fragment). The fragment was ligated with the vector, and the ligation product was transformed into DH5α E. coli, and a positive clone was picked out. After sequencing analysis, the positive plasmid with Kpn I+Bam HI was digested and purified as cloning vector. The upstream long arm DNA fragment with Kpn I+Bgl II was digested, the 3.4 kb DNA fragment was purified and inserted to the above vector, then was transformed into DH5α E. coli; and a positive clone was picked out. The positive plasmid with Xho I+Not I was digested and purified after electrophoresis as cloning vector. The downstream short arm DNA fragment with Sal I+Not I was digested, ligated the fragment with the vector after purification using electrophoresis, and obtained the targeting vector pm-hNGF (FIG. 1B). FIG. 1C shows the process of construction. After confirmation by sequencing, the constructed vector will be used in gene targeting.

Example 2

Construction of a Mutant NGF Targeting Vector

This example changed three amino acids of mouse NGF-β mature peptide.

1) The Following Primers were Synthesized:

P2' 5'ggaagactgggtgggtggatgagcgcttgctccggtgagt 3'    (SEQ ID No. 9)

P3' 5'actcaccggagcaagcgctcatccacccacccagtatccacatgggggg 3' (SEQ ID No. 10)

P4' 5'gggctgcaggcaagtcagcctcttcttgtagcctt 3'    (SEQ ID No. 11)

P5' 5'aaggctacaagaagaggctgacttgcctgcagccccttccccacct 3' (SEQ ID No. 12)

2) Construction of a Mutant NGF:

By using mouse genomic DNA (1 μg) as template, P3'+P4' as primers (100 ng each), Pfu high fidelity polymerase (2.5 U), 250 μmol/L dNTPs, 2.5 mmol/L MgCl2 and 25 mmol/L Tris HCl (pH8.3), the PCR reaction (94° C. 30 s, 55° C. 30 s, 72° C. 45 s, 30 cycles, Perkin Elmer 9700 PCR Amplifier) was performed. The PCR product was purified by using a Qiagen Gel Extraction Kit (from QIAGEN) after electrophoresis in 1% agarose and DNA fragment of about 0.37 kb was obtained. By using this DNA fragment as template, Lys32, Lys34 and Glu35 in NGF mature peptide were changed to Ala by using Stratagen Point Mutation Kit (for details, see the instruction of Stratagen Point Mutation Kit).

3) Construction of an Upstream Long Arm:

By using mouse genomic DNA (1 μg) as template, P1+P2' as primers (100 ng each), Pfu high fidelity polymerase (2.5 U), 250 μmol/L dNTPs, 2.5 mmol/L MgCl2 and 25 mmol/L Tris-HCl (pH8.3), a PCR reaction (94° C. 30 s, 55° C. 30 s, 72° C. 4 min, 30 cycles, Perkin Elmer 9700 PCR Amplifier) was performed. The PCR product was purified by using a Qiagen Gel Extraction Kit (from QIAGEN) after electrophoresis in 1% agarose, and then DNA fragments of 4.4 kb was obtained. Under the same conditions as above, a PCR reaction was performed by using mouse genomic DNA (1 μg) as template and P5'+P6 as primers (100 ng each) as primers, 0.65 kb DNA fragments were obtained, and the isolation and purification were performed by using the same agarose electrophoresis as above. The two above-mentioned DNA fragments and the mutant NGF fragment (100 ng each PCR product) were mixed as PCR template and a PCR reaction (under the same condition as above except the extension time at 72° C. is 5 minutes) was performed by using P1+P6 as primers (100 ng each), 5.4 kb DNA fragments were obtained, and the isolation and purification were performed by using the same agarose electrophoresis as above.

4) Construction of a Downstream Short Arm: Same as Example 1.

Figure 2A:
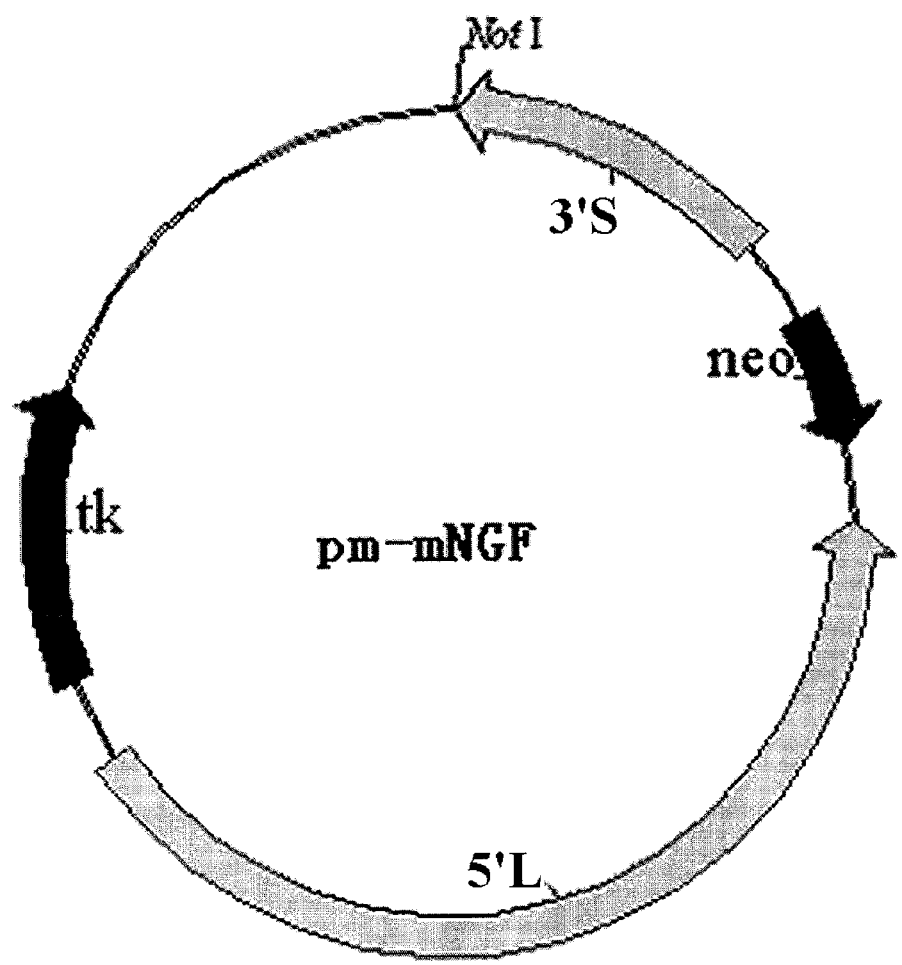
FIG. 2A is the schematic diagram showing the structure of targeting vector pm-mNGF.
Figure 2B:
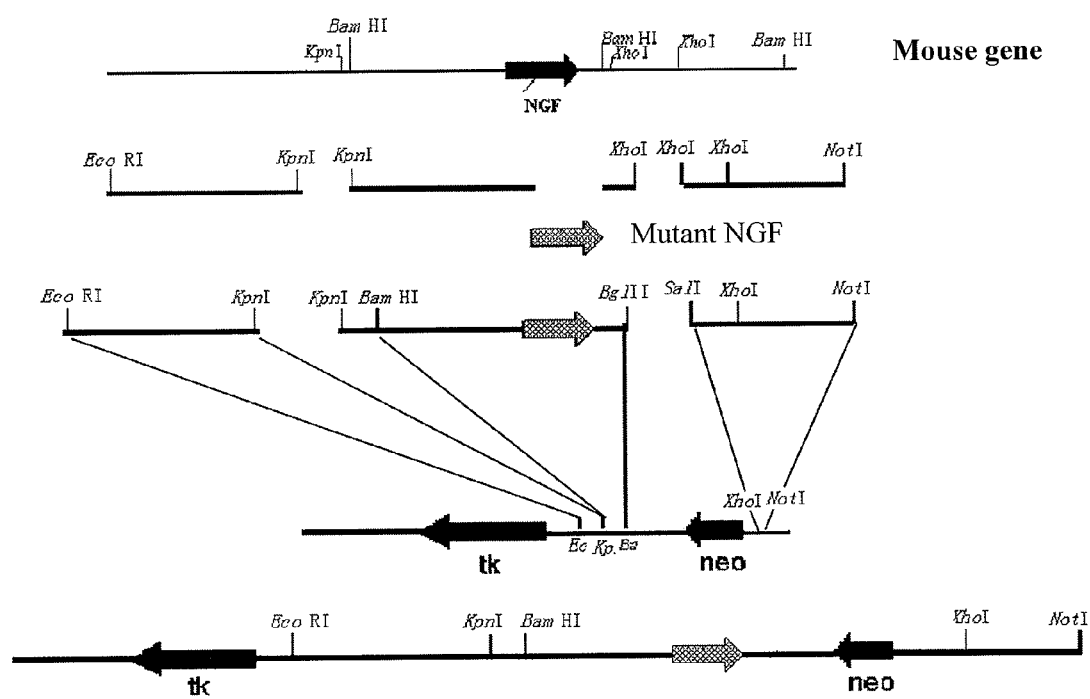
FIG. 2B is the schematic diagram showing the process of constructing the targeting vector pm-mNGF.

5) Construction of a Targeting Vector:

The pLoxPneo vector with Eco RI+Kpn I (Biolabs, hereinafter using the same) was digested and then purified. The upstream long arm DNA fragment with EcoR I+Kpn I was digested and the 2.06 kb DNA fragment was purified. The fragment with the vector were ligated, the ligation product was transformed into DH5α E. coli, and a positive clone was picked out. After sequencing, the positive plasmid with Kpn I+Bam HI was digested and purified as a cloning vector. The upstream long arm DNA fragment with Kpn I+Bam HI was digested; the 3.4 kb DNA fragment was purified and inserted to the above vector, and then was transformed into DH5α E. coli, and a positive clone was picked out. After sequencing, he positive plasmid with Xho I+Not I was digested and purified as a cloning vector using electrophoresis. The downstream short arm DNA fragment with Sal I+Not I was digested, inserted into the vector after purification and a targeting vector pm-mNGF was obtained (FIG. 2A). (FIG. 2B shows the process of the construction.) After sequencing confirmation, the constructed vector will be used in the gene targeting.

Example 3

The Mouse Embryonic Stem Cells Knock-In Human NGF Mature Peptide Gene was Obtained 1) The Culture and Treatment of Trophoblast:

Mouse primary fibroblasts were thawed into two 100 mm dishes, trophoblast medium (DMEM, 15% FBS, 0.1 mM β-mercaptoethanol, 0.1 mmol/L ampicillin-streptomycin, 0.1 mmol/L L-glutamine, 0.1 mM non-essential amino acids) was added and the cells were incubated at 37° C. in a $CO_2$ incubator containing $CO_2$ of 0.05%. After three days, these cells were digested with trypsin and transferred to six 150 mm tissue culture dishes. Three days later, these cells were transferred to forty 150 mm tissue culture dishes and continued being cultured for 3 to 4 days until the bottom of the dishes were covered with cells. The fibroblasts was treated with Mitomycin C (final concentration: 10 μg/ml) and the cells were incubated at 37° C. for 2 to 3 h. The fibroblasts treated with Mitomycin C were frozen and losing mitotic activity, and then were formulated into the trophoblast.

2) Transfection of ES Cells by Electroporation:

After forming the trophoblast, 129/ter mouse embryonic stem cells on trophoblast were inoculated and the cells were cultured with trophoblast medium with the presence of 1000 U/ml LIF. The cells were treated with 1 ml 0.25% trypsin, then washed with 3.5 ml ES cell culture medium and suspended in PBS. 50 μg Not I linearized pm-hNGF plasmid was mixed with 1 ml above-mentioned ES cell mixture. The cells were transfected by using gene pulser system (Biorad) 600V, 25 μF. One minute later at room temperature, 7 ml ES cell culture medium were added and the cells were transferred to four dishes covered with trophoblast. After letting the cells grow for 24 hours, 280 μg/ml G418 and 2 μmol/L gancyclovir were added and continued being cultured for seven days (change the medium everyday). Then the clones were picked out.

Figure 3A:
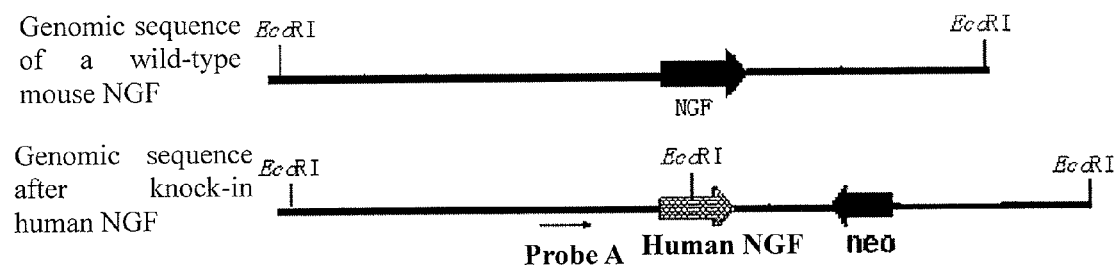
FIG. 3A is the schematic diagram showing the comparison of a wild-type mouse NGF-β genomic sequence with the genomic sequence of mouse embryonic stem cell target knock-in human NGF-β mature peptide gene.
Figure 3B:
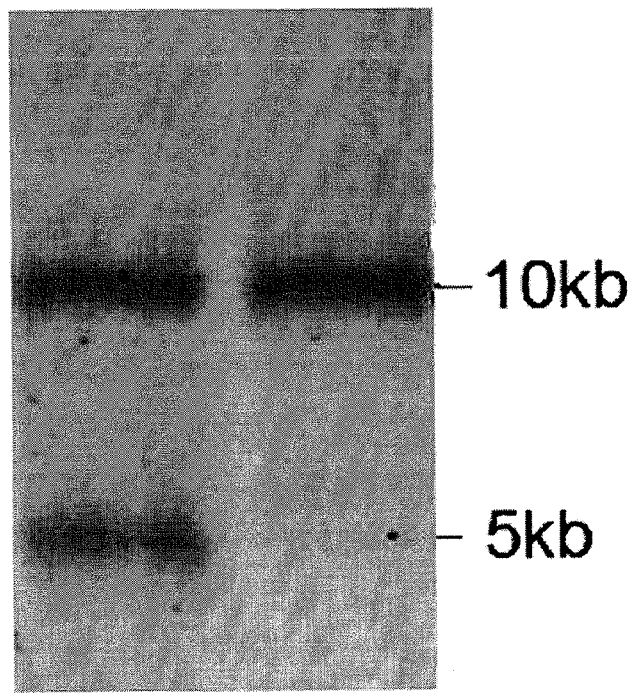
FIG. 3B is the photograph showing the Southern blotting result of embryonic stem cells of a wild-type mouse and those of a mouse knock-in human NGF-β mature peptide, wherein Ec represents an EcoR I digested fragment; T represents the embryonic stem cell of a mouse knock-in human NGF-β mature peptide; and WT represents the embryonic stem cell of a wild-type mouse.

3) Characterization of the Embryonic Stem Cells Knock-in Human NGF Mature Peptide Mouse (1) Southern Blotting:

As shown in FIG. 3A, the genomic DNA of ES cells and G418/FIAU double resistant clone were extracted, and digested with EcoR I; and then southern blotting was performed by using the probe a of 5' end targeting vector. There was only one band about 10 kb in wild-type cells compared with the recombinant ES cells which show another band about 5 kb (see FIG. 3B) because of the EcoR I site in human NGF mature peptide gene.

Figure 4A:
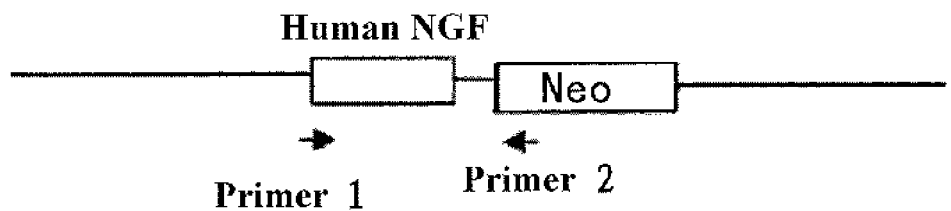
FIG. 4A is a schematic diagram showing the embryonic stem cell of a mouse knock-in human NGF-β mature peptide.
Figure 4B:
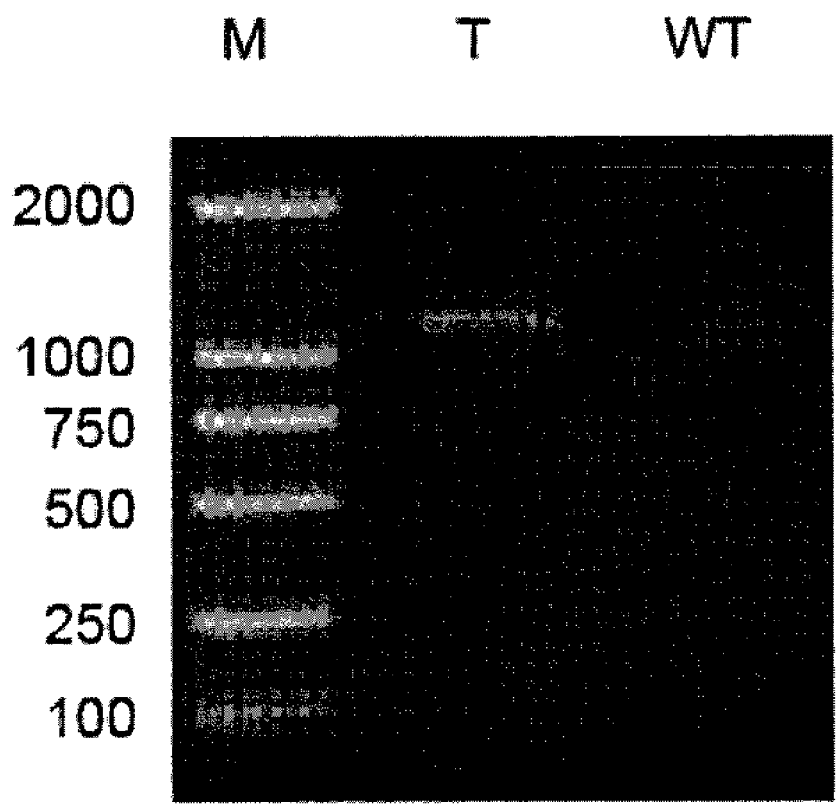
FIG. 4B is the photograph showing the PCR result of a mouse knock-in human NGF-β mature peptide, wherein M represents standard molecular weight marker, T represents the embryonic stem cell of knock-in mouse, and WT represents the embryonic stem cell of a wild-type mouse.

(2) PCR Characterization:

As shown in FIG. 4A, primer 1 (5'gctcatcctcccatcccatcttc-caca 3' (SEQ ID No. 13)) locates at the 5' end of the mature peptide, and primer 2 (5'gaacgagatcagcagcctctgttc ca 3' (SEQ ID No. 14)) locates at Neo gene. When using primer 1 and primer 2 to amplify the genome, there is not any band in wild-type ES cells. But in recombinant ES cells, there is a band about 1200 bp amplified (FIG. 4). The PCR product was verified by EcoR I digestion and DNA sequencing, and confirmed that the NGF mature peptide gene in mouse genome has already been replaced with that of human genome.

Example 4

Construction of the Mouse Embryonic Stem Cells Knock-in Mutant NGF

1) The method to construct mutant NGF knock-in mouse embryonic stem cells is the same as Example 3.

Figure 5A:
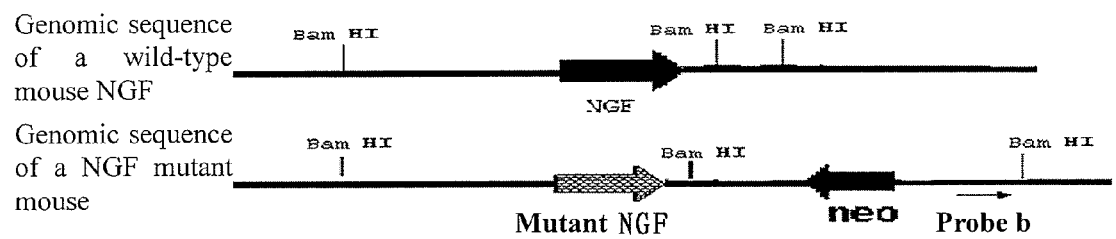
FIG. 5A is a schematic diagram showing the comparison between the genomic sequence of a wild-type mouse NGF-β with the genomic sequence of a mouse knock-in mutant NGF-β.
Figure 5B:
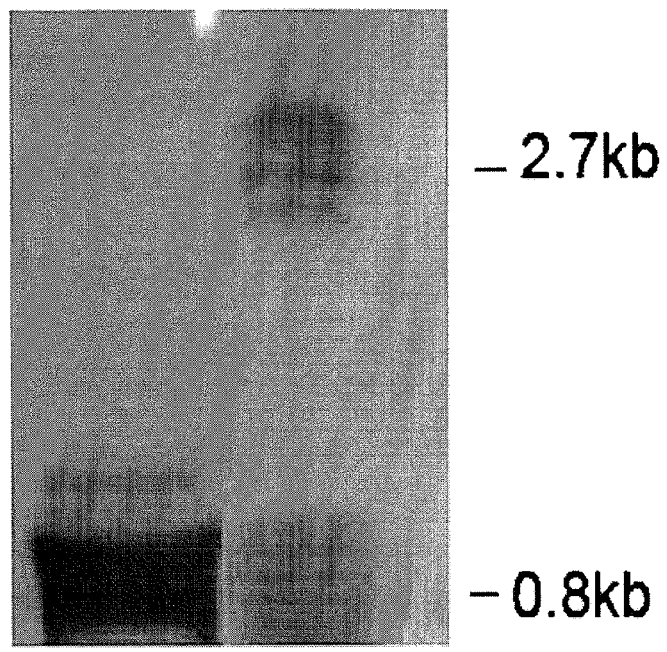
FIG. 5B is the photograph showing the Southern blotting result identifying the embryonic stem cell of a wild-type mouse and a mouse knock-in mutant NGF-β, wherein, Ba represents the BamH I digested fragment, T represents the embryonic stem cell of knock-in mouse, and WT represents the embryonic stem cell of a wild-type mouse.

2) The characterization of mouse embryonic stem cells knock-in mutant NGF:

(1) Southern Blotting:

As shown in FIG. 5A, the genomic DNA of ES cells and G418/FIAU double resistant clone were extracted, and the genomic DNA was digested with BamHI. And then southern blotting was performed by using probe b of the 5' end downstream of the homology arm. There was only one band about 800 bp in wild-type cells when compared with the recombinant ES cells, which showed a band about 2.7 kb (FIG. 5B). This is due to the insertion of the Neo gene between the two BamH I site.

(2) PCR Characterization:

Primer 1 (5'gctcatccacccacccagtcttcca ca 3' (SEQ ID No. 15)) which locates in the 5' end of the NGF mature peptide and primer 2 (5'gaacgagatcagcagcctctgttcca 3' (SEQ ID No. 16)) which locates in the Neo gene was designed. When using primer 1 and primer 2 to amplify the genome, there is not any band in wild-type ES cells. But in recombinant ES cells, there is a band about 1200 bp amplified. The PCR product was verified by DNA sequencing, and was confirmed that the NGF mature peptide gene in mouse genome has already been replaced with the mutant gene.

Example 5

Construction of a Human NGF Gene Knock-in Mouse

1) Preparation of Donor Blastocyst:

4- to 6-week-old C57BL/6J anestrous female mice were selected, intraperitoneally injected 5 units of pregnant mare serum gonadotropin; and after 48 hours intraperitoneally injected 5 units of human chorionic gonadotropin and then were transferred to cages of adult male mice for mating. The mice after 48 hours were checked, and set up a new cage for those having vaginal plugs. On the 4th day after mating, the donor female mice were sacrificed by cervical dislocation; the uterus was exposed, and the two uteri at the connective area between the Fallopian tubes with uterine horns were cut out by using a pair of scissors, and then the linked section of uterus were carefully cut off, and placed on a sterile 60 mm Petri dish. And the Fallopian tubes and uterine horns respectively at uterine head side and end side were clipped off by using a pair of scissors, which made two separate uteri unimpeded. By using a disposable syringe full of Brinster's BMOC-3 (GIBCO BRL) medium with 5# needle, and, while viewing under stereo microscope, the syringe was insert into the uterine cavity, pushing the syringe plug to flush out the uterine cavity, and mouse embryos were settled quickly to the bottom of Petri dish. A 35 mm dish was gotten, some culture medium was dropped, and the surface was covered with mineral oil. The embryos were collected by flushing under a stereo microscope, and transferred to medium drop, then incubated in at 37° C., 5% in a $CO_2$ incubator for 2 hours.

2) Microinjection of Blastocyst:

ES cells for injection were thawed several days before use, changed for fresh ES cell culture medium on the morning of injection, trypsinized after 1 to 2 hours, then kept in Brinster's BMOC-3 medium as single-cell suspension. From a 35 mm Petri dish, about 10 blastocysts exhibiting full form, a clear border and a visible blastocoel cavity were select, and then transferred to an injection groove which has been installed with an ovum-holding tube and injection needle. 10 to 15 small, round ES cells were loaded into injection needle under a 10× lens, and then were aspirated one side of the blastocyst by holding pipette under 40× lens, adjusting the injection needle to a position targeting to the center of blastocyst and in a same horizontal. The injection needle's joystick was rotated, by using the needle's tip to quickly puncture the wall of the blastocyst and enter the blastocoel, the injection pump was pushed to expel ES cells into the blastocoel in sequence, and then the needle was carefully withdrawn. According to the condition of the mouse blastocysts and the number of recipient mice, the number of blastocysts to inject was determined. Blastocysts, after injection, were cultured in droplets of Brinster's BMOC-3 medium.

3) Transfer of Embryos to Recipient Uterus

The recipient mice, Kunming pseudopregnancy white mice, were females mated with vasectomized males. The recipient's back was sterilized with ethanol, and then made a transverse incision of about 1 cm length on the right side just near the first lumbar. Drew on both sides until the right ovary and its fat pad appear through the peritoneum. A 3 mm rip in the peritoneum was torn with tweezers. The fat pad was grasped and pulled out with the operator's left hand, after which the uterus was visible. A small hemostatic forceps were attached to a little bit of the fat pad for slight fastening. A mouth-controlled pipette was put onto a transfer pipette. Then, under a stereo microscope, the culture in the following sequence were carefully aspirated: medium, bubbles, medium, bubbles, the injected blastocyst, bubbles, and a small amount of medium. The operator held tweezers with his left hand to grasp the uterus wall 2 mm from the interface of uterus and Fallopian tubes, while he held a 4# needle syringe and transfer pipette with his right hand. Under the anatomical lens, the needle was used to make a small hole near the tweezers (while avoiding the vessel), then the tip of the transfer pipette was inserted into the small hole. The embryos were gently blown into the uterus. The uterus and mesentery were pushed back into the abdominal cavity, then the incision was sutured. (See, Gene Targeting Technology, p 133, Xiao Yang, et. al., by Science Press).

4) Gain of Transgenic Mice

The transplant surgery was successful, small mice were born after 17 days, and a few days later, were estimated whether a chimera mouse of high chimerism has been obtained from color patterns. Said high-chimerism mice, when selected to mate with C57BL/6J mice, in the offspring pure brown transgenic heterozygous mice were obtained. Mating among these heterozygous mice can screen out homozygous transgenic mice.

Example 6

Construction of a Mouse Knock-In NGF-β Gene

The method's details are the same as Example 5.

Example 7

Identification of a Mouse Knock-In Human NGF-β Mature Peptide

1) Preparation of Mouse Genomic DNA:

About 0.5 cm of a tail was cut from a 15-day-old mouse and was put to an Eppendorf tube. 400 µl tail lysis buffer (0.5% SDS, 0.1M NaCl, 0.05M EDTA, 0.01M Tris-HCl pH8.0, 200 µg/ml proteinase K) was added to each tube and the tubes were incubated at 50° C. overnight. 200 µl saturated NaCl (6M) was added to each tube, vortexed vigorously and stood on ice for 10 minutes. The tubes were centrifuged at 14,000 rpm for 10 minutes at room temperature and transferred the supernatant of each tube to a new Eppendorf tube. 0.8 ml ethanol was added to each tube and they were mixed well. The tubes then were centrifuge at 14,000 rpm for 5 minutes and the supernatant was discarded. The pellets were allowed to dry and the DNA in each tube was dissolved in 50 to 100 µl TE.

Figure 6A:
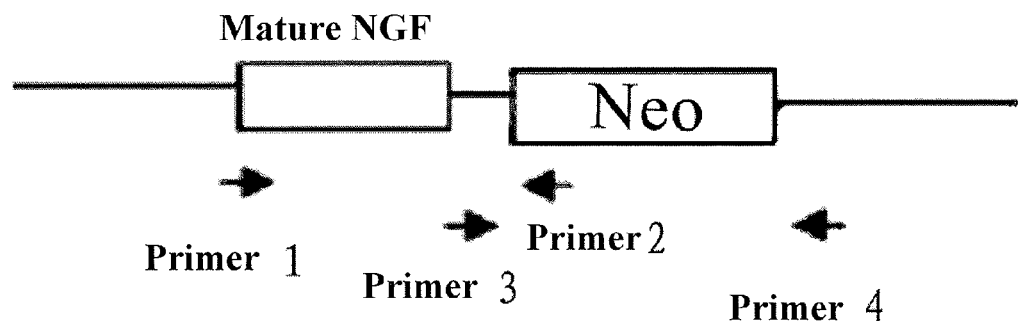
FIG. 6A is the schematic diagram showing the process of genotype identification of a mouse knock-in human NGF-β by PCR.
Figure 6B:
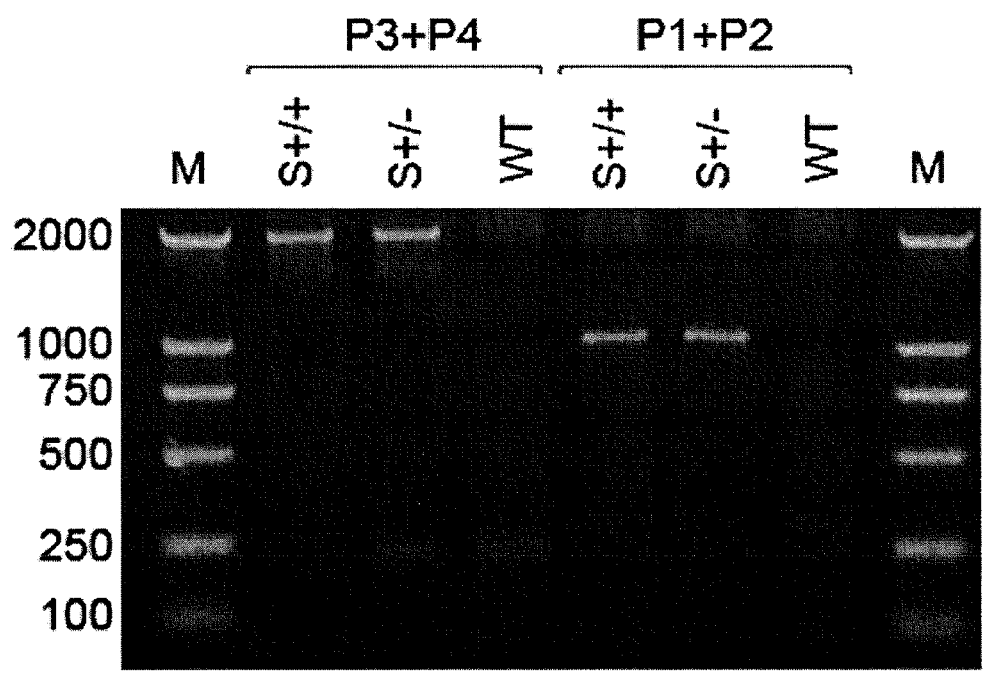
FIG. 6B is the schematic diagram showing the comparison of PCR-SDS PAGE for the genotype identification of a wild-type C57BL/6J mouse, human NGF-β heterozygote transgenic mouse and human NGF-β homozygote transgenic mouse, wherein, M represents standard molecular weight marker, S+/+ represents homozygote transgenic mouse, S+/− represents heterozygote transgenic mouse, and WT represents a wild-type mouse.

2) Genotype Identification of Mouse by PCR:

As shown in FIG. 6A, primer 1 (5' acaggactcaccggag-caagcgctcat 3' (SEQ ID No. 17)) locates in the 5' end of the mature peptide; primer 2 (5'gaacgagatcagcagcctctgttcca3' (SEQ ID No. 18)) locates in Neo gene; primer 3 (5'gaactc-ccagtgtggataagtaga3' (SEQ ID No. 19)) locates in none coding region downstream mature peptide gene; primer 4 (5'aat-agtagagaagcagccatcagagca3' (SEQ ID No. 20)) locates in 5'end of downstream homology arm. By using mouse genomic DNA (1 µg) as template, primer 1+primer 2 as primers (100 ng each), Pfu high fidelity polymerase (2.5 U), 250 µmol/L dNTPs, 2.5 mmol/L MgCl2 and 25 mmol/L Tris-HCl (pH8.3), PCR reaction (94° C. 30 s, 55° C. 30 s, 72° C. 1 min, 30 cycle, Perkin Elmer 9700 PCR amplifier) was performed. After the electrophoresis of PCR product in 1% agarose, there is not any specific amplified band in the wild-type C57BL/6J mouse. But in heterozygote and homozygote transgenic mouse, there was a band about 1200 bp amplified. The PCR product was verified by DNA sequencing and confirmed that the NGF mature peptide gene in mouse genome has already been replaced by the human gene. A PCR reaction was performed by using primer 3+primer 4 (100 ng each) (under the same condition as above except the extension at 72° C. is 2 min). After electrophoresis of PCR product in 1% agarose, there is a band about 190 bp in a wild-type C57BL/6J mouse; In heterozygote mouse, there is another band about 2000 bp besides the 190 bp bands; As for homozygote mouse, there is only one band about 2000 bp.

3) Gene Sequencing of NGF Mature Peptide Gene in Homozygote Mouse:

About 0.5 cm tail was cut from homozygote mouse and was put to an Eppendorf tube. 400 µl tail lysis buffer (0.5% SDS, 0.1M NaCl, 0.05M EDTA, 0.01M Tris-HCl pH8.0, 200 µg/ml proteinase K) was added and the tubes were incubated at 50° C. overnight. 200 µl saturated NaCl (6M) was added into each tubes; the tubes were vortexed vigorously and put on ice for 10 minutes. The tubes were centrifuge at 14,000 rpm for 10 minutes at room temperature and the supernatant of each tube was transferred to a new Eppendorf tube. 0.8 ml ethanol was added to each tube and they were mixed well. The tubes were centrifuged at 14,000 rpm for 5 minutes, and then the supernatant was discarded. The pellets were allowed to dry, and then the DNA in each tube was dissolved in 50 to 100 µl TE.

The primer (5'AATCCCTTTCAACAGGACTCACCG-GAG CAA 3' (SEQ ID No. 21)) and primer (5'AAGGGGGCTGCAG GCAAGTCAGCCTCTTC 3' (SEQ ID No. 22)) to upstream and downstream, respectively, of the NGF mature peptide gene were designed. By using mouse genomic DNA (1 µg) as template, Pfu high fidelity polymerase (2.5 U), a PCR reaction (94° C. 30 s, 55° C. 30 s, 72° C. 1 min, 30 cycle, Perkin Elmer 9700 PCR amplifier) was performed. After electrophoresis in 1% agarose and TA cloning, the PCR product was sequenced. The result shows that the mature peptide gene is human NGF-β gene. The sequence is as follows

```
                                          (SEQ ID No. 23)
TCATCATCCCATCCCATCTTCCACAGGGGCGAATTCTCGGTGTGTGA

CAGTGTCAGCGTGTGGGTTGGGGATAAGACCACCGCCACAGACATCAA

GGGCAAGGAGGTGATGGTGTTGGGAGAGGTGAACATTAACAACAGTGT

ATTCAAACAGTACTTTTTTGAGACCAAGTGCCGGGACCCAAATCCCGTT

GACAGCGGGTGCCGGGGCATTGACTCAAAGCACTGGAACTCATATTGTA

CCACGACTCACACCTTTGTCAAGGCGCTGACCATGGATGGCAAGCAGG

CTGCCTGGCGGTTTATCCGGATAGATACGGCCTGTGTGTGTGTGCTCAGC

AGGAAGGCTGTGAGAAGAGCCTGA
```

Figure 7A:
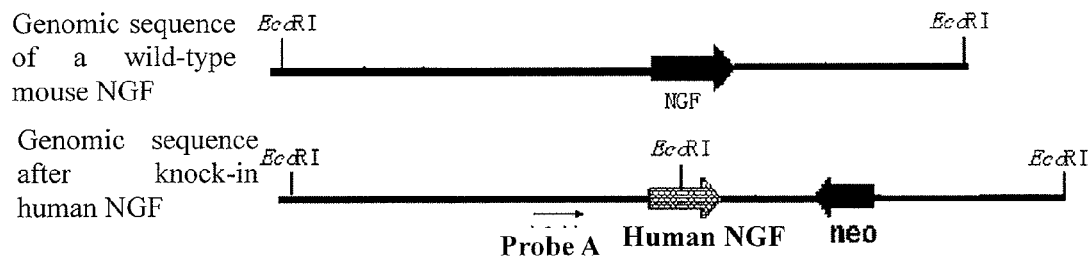
FIG. 7A is the schematic diagram showing the comparison of the genomic sequence of a wild-type mouse NGF-β and the genomic sequence of a mouse knock-in human NGF mature peptide.
Figure 7B:
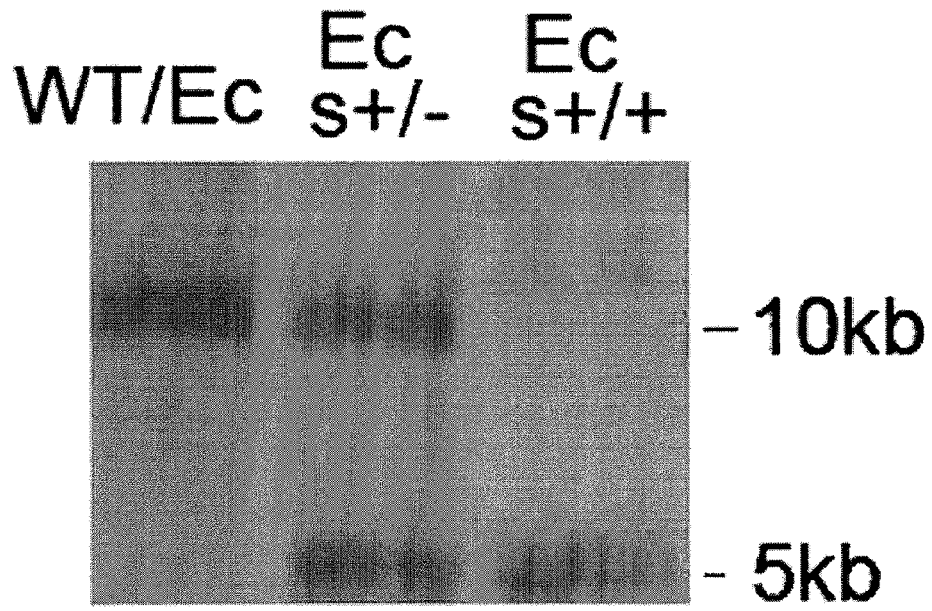
FIG. 7B is the schematic diagram showing the comparison of the Southern blotting result of a wild-type C57BL/6J mouse, a human NGF-β heterozygote transgenic mouse and human NGF-β homozygote transgenic mouse, wherein Ec represents the EcoR I digested fragments, S+/+ represents homozygote transgenic mouse, S+/− represents heterozygote transgenic mouse, and WT represents a wild-type mouse.

4) Southern Blotting Identification:

As shown in FIG. 7A, the mouse-tail genomic DNA was extracted and digested with EcoR I. A southern blotting was performed by probe a of 5' end of targeting vector. There is a band of about 10 kb in a wild-type C57BL/6J mouse. Because of the EcoR I site in the human NGF mature peptide gene, in the heterozygote mouse, there is another band about 5 kb besides the 10 kb band. While in homozygote mouse, there is only one 5 kb band. (FIG. 7B)

Example 8

Identification of Mouse Knock-In Mutant NGF-β Gene

1) PCR Identification and the Results are the Same as Example 7.

2) Gene Sequencing of NGF Mature Peptide Gene in Homozygote Mouse:

About 0.5 cm of tail was cut from a homozygote mouse and was put into an Eppendorf tube. 400 µl tail lysis buffer (0.5% SDS, 0.1M NaCl, 0.05M EDTA, 0.01M Tris-HCl pH8.0, 200 µg/ml proteinase K) was added and the tubes were incubated at 50° C. overnight. 200 µl saturated NaCl (6M) was added to each tube; the tubes were vortexed vigorously and stood on ice for 10 minutes. The tubes then were centrifuge at 14,000 rpm for 10 minutes at room temperature and the supernatant of each tube was transferred to a new Eppendorf tube. 0.8 ml ethanol was added to each tube and they were mixed well. The tubes were centrifuge at 14,000 rpm for 5 minutes and the supernatant was discarded. The pellets were allowed to dry, and the DNA of each tube was dissolved in 50 to 100 µl TE.

Primer (5' AATCCCTTTCAACAGGACTCACCGGAG CAA 3' (SEQ ID No. 24)) and primer (5' AAGGGGGCTG-CAGG CAAGTCAGCCTCTTC 3' (SEQ ID No. 25)) to upstream and downstream, respectively, of the NGF mature peptide gene were designed. By using mouse genome DNA (1

µg) as template, Pfu high fidelity polymerase (2.5 U), a PCR reaction (94° C. 30 s, 55° C. 30 s, 72° C. 1 minute, 30 cycle, Perkin Elmer 9700 PCR amplifier) was performed. After electrophoresis of PCR product in 1% agarose and TA cloning, the PCR product was sequenced. The result shows that the mature peptide gene is mouse mutant NGF-β gene. The sequence is as follows:

(SEQ ID No. 26)
TCATCCACCCACCCAGTCTTCCACATGGGGGAGTTCTCAGTGTGTG

ACAGTGTCAGTGTGTGGGTTGGAGATAAGACCACAGCCACAGACATCG

CCGGCGCGGCTGTGACAGTGCTGGCCGAGGTGAACATTAACAACAGTG

TATTCAGACAGTACTTTTTTGAGACCAAGTGCCGAGCCTCCAATCCTGT

TGAGAGTGGGTGCCGGGGCATCGACTCCAAACACTGGAACTCATACTG

CACCACGACTCACACCTTCGTCAAGGCGTTGACAACAGATGAGAAGCA

GGCTGCCTGGAGGTTCATCCGGATAGACACAGCCTGTGTGTGTGCTC

AGCAGGAAGGCTACAAGAAGAGGCTGA

Figure 8A:
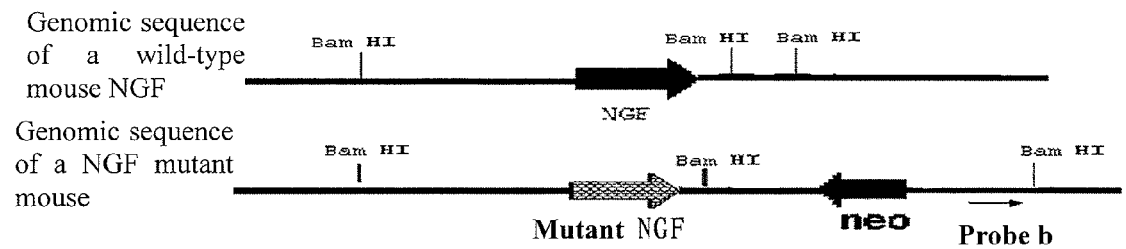
FIG. 8A is the schematic diagram showing the comparison between the genomic sequence of a wild-type mouse and the genomic sequence of the mouse knock-in mutant NGF-β.
Figure 8B:
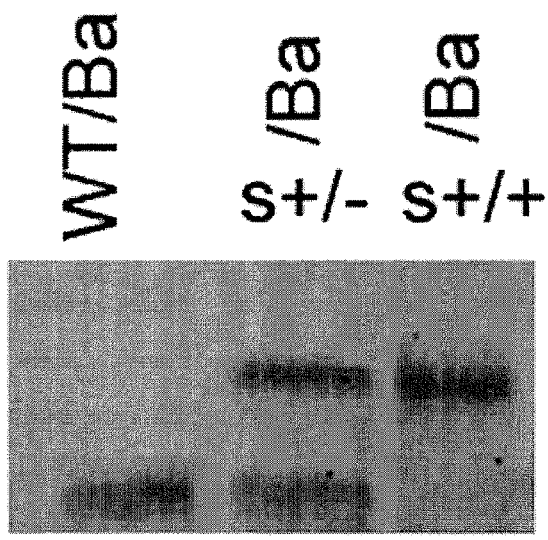
FIG. 8B is the schematic diagram showing the comparison of the Southern blotting result of a wild-type C57BL/6J mouse, Mutant NGF-β heterozygote transgenic mouse and the Mutant NGF-β homozygote transgenic mouse, wherein Ba represents the BamH I digested fragment, S+/+ represents homozygote transgenic mouse, S+/− represents heterozygote transgenic mouse, and WT represents a wild-type mouse.

3) Southern Blotting Identification:

As shown in FIG. 8A, the mouse tail genome DNA was extracted and digested with BamH I. The southern blotting was performed by probe b of 5'end downstream the homology arm. There is a band about 800 bp in a wild-type C57BL/6J mouse. After mutant NGF-β recombination, the neo gene is inserted between the two BamH I sites, so there is another band about 2.7 kb in the heterozygote mouse. As for the homozygote mouse, there is only one 2.7 kb band. (FIG. 8B)

Example 9

Extraction of NGF from the Submandibular Glands of a Mouse Knock-In Human NGF Mature Peptide 1) Extraction:

In Grade I Lab, a healthy male mouse (weight: 30 to 40 g) was killed by cervical dislocation, and the submandibular glands were immediately collected. Pure water was added by 1:2 to 1:5 (g:ml) and the tissue was ground with a high-speed grinder. The mixture was diluted with pure water by 2 to 3 times and centrifuged at 12,000 rpm for 1 hour. The supernatant was collected and dialyzed in 0.02M pH6.8 PB. The sample was loaded onto a CM-Sepharose FF Chromatography Column fully pre-balanced with 0.02M pH6.8 PB. The column was washed with balance buffer and the eluted protein solution was collected. The protein solution was dialyzed in 0.25 mM pH6.8 PB for 24 h, during which the dialysis buffer was changed 2 or 3 times. The pH is decreased to 4.0 by adding 1M acetic acid buffer (pH4.0) to the protein solution after dialysis. 0.4M NaCl was added and stood still for 5 minutes. The solution was centrifuged at 10000 g for 30 minutes, and then the supernatant was collected. The supernatant was loaded onto a CM-Sepharose FF Chromatography Column fully balanced with 0.05M pH4.0 acetic acid buffer (containing 0.4M NaCl) beforehand. The column was washed with balance buffer to baseline. The column was washed again with 0.05M pH9.0 Tris buffer until the impurity peak reaches the baseline, then gradually washed with 0 to 0.4M NaCl and the protein peak desired was collected. After gel filtration chromatography (Superdex G75 prep grade column balanced with 0.05M pH9.0 Tris (containing 0.15M NaCl)), the protein solution was filtered with a filter membrane (20 nm aperture) to remove the virus. The filtrate was collected.

2) Identification by Electrophoresis.

Figure 9:
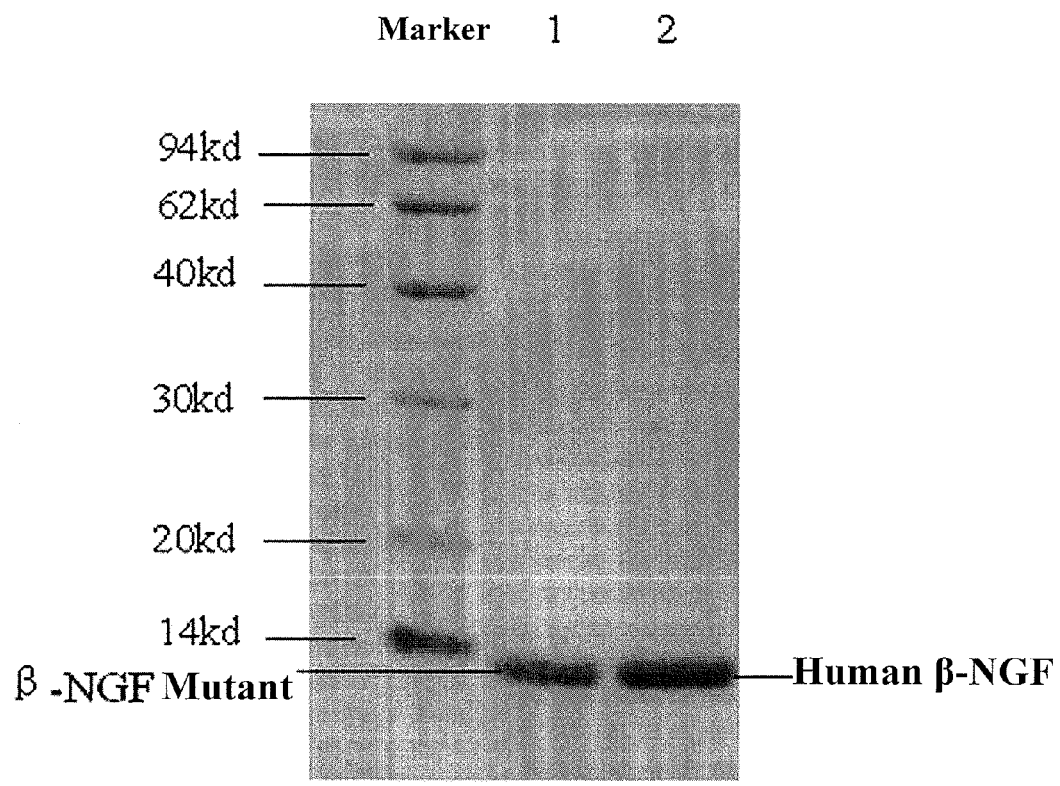
FIG. 9 is the schematic diagram showing the molecular weight of the extracted protein using SDS-PAGE.
Figure 10:
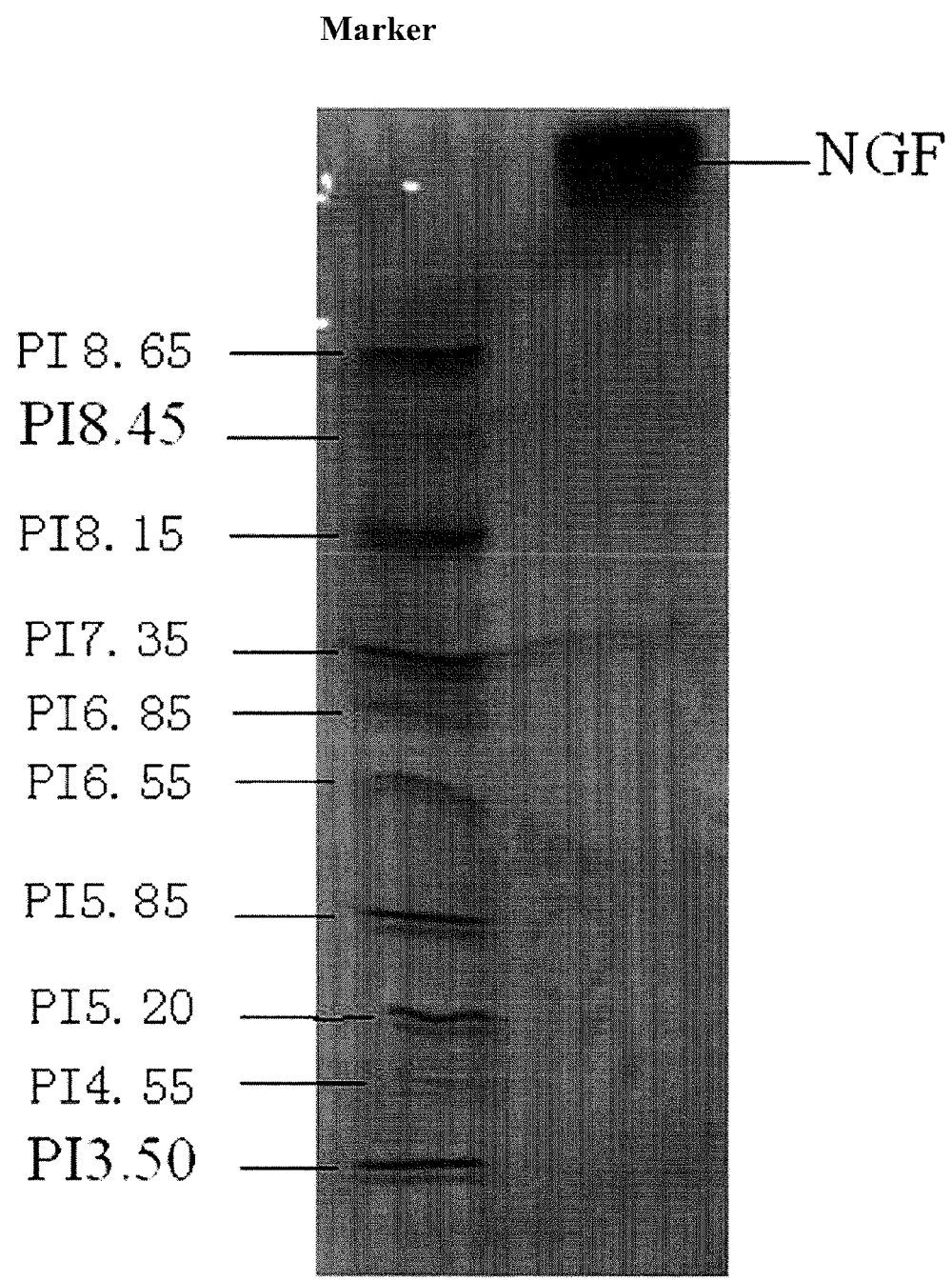
FIG. 10 is the schematic diagram showing the result of the extracted protein using isoelectric focusing electrophoresis.

SDS-PAGE was used to examine the molecular weight of the protein (the result is shown in FIG. 9). The PI is measured by using isoelectric focusing (the result is shown in FIG. 10).

Example 10

Extraction of NGF from the Submandibular Glands of Mouse Knock-In Mutant NGF

The methods are the same as Example 9. SDS-PAGE results are shown in FIG. 9.

Example 11

Measurement of the Relative Activity of Human NGF and further the Identification of Protein Extracted in Example 9

Method: chicken embryo dorsal root ganglia culture measurement:

The bottom of culture flask was coated with mucilage mouse glue, dried and washed twice with DMEM containing 10% FCS. 3 ml DMEM was added and balanced overnight. The medium was discarded just before use. The dorsal root ganglions (DRG) from a chicken embryo (age 8 days) were inoculated in a flask filled with mucilage mouse glue (3-5 ganglions in each flask). The flasks was put in an incubator (5% $CO_2$) and incubated for 2 hours at 37° C. The NGF sample was gradually dilute and the dilution was added to the flasks.

Figure 11:
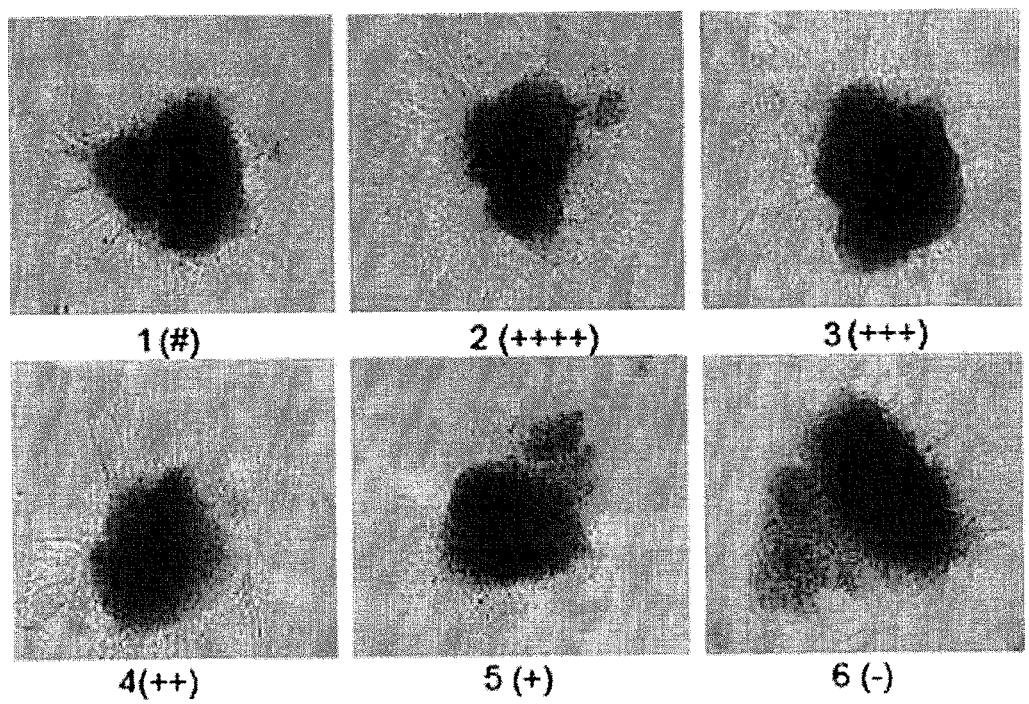
FIG. 11 is the schematic diagram showing the relative activity of extracted human NGF.

The judgment criterion of the results: "−" represents no neurite outgrowth; "+" represents a little neurite outgrowth. Long neurite outgrowths, if there are many, can be represented by "++" to "+++" depending on the density and length, while "++++" represents the densest one and "#" represents over-inhibition. The amount (per ml) of sample with the densest and longest outgrowth is used as the activity unit. The result is shown in FIG. 11, which shows the differentiation of DRG induced by recombinant human NGF. 1: 27 ng/ml NGF; 2: 9 ng/ml NGF; 3: 3 ng/ml NGF; 4: 1 ng/ml NGF; 5: 0.33 ng/ml NGF; 6: negative control, DRG is cultured in DMEM).

Example 12

Figure 12:
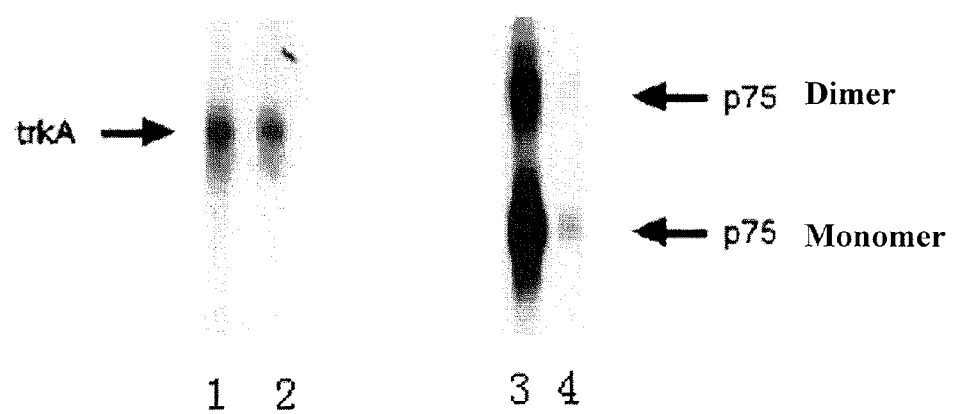
FIG. 12 is the schematic diagram showing the receptor binding result of extracted mutant NGF-β.

Identification of the Biological Characteristics of Mutant NGF and the Measurement of its Activity 1) Receptor Binding Experiment of Mutant NGF:

The WT mouse NGF and mutant NGF was labeled with $I^{125}$, then added to both the cells expressing TrkA and the A875 tumor cells expressing P75. The ligand and receptor were crosslinked by N-hydroxysuccinimidyl-4-azidobenzoate, the cells were lysed, and the cross-linked complex was immunoprecipitated overnight at 4° C. After SDS-PAGE and autoradiography, results show that both WT NGF and mutant NGF can bind TrkA, while the mutant NGF cannot bind P75. (FIG. 12 shows the autoradiography results. 1: TrkA-WT NGF complex; 2: TrkA-NGF mutant complex; 3: P75-WT NGF complex; 4. P75-NGF mutant complex).

2) Measurement of Mutant NGF Relative Activity

Method: chicken embryo dorsal root ganglia culture measurement:

The bottom of a culture flask was coated with mucilage mouse glue, then dried and washed twice with DMEM containing 10% FCS. 3 ml DMEM was added and balanced overnight. The medium was discard before use. The dorsal root ganglions (DRG) from a chicken embryo (age 8 days) were inoculated in the flask filled with mucilage mouse glue (3-5 ganglions each flask).

The judgment criteria for the results are as follows: "−" represents no neurite outgrowth; "+" represents a little neurite outgrowth. Long neurite outgrowths, if there are many, can be represented by "++" to "+++" depending on the density and length. The symbol "++++" represents the densest one, and "#" represents over-inhibition. The results show that, at high concentration, mutant NGF has the same ability as WT NGF in inducing the growth of ganglion (27 ng/ml, 9 ng/ml). At low concentration, however, this ability decreases obviously (3 ng/ml, 1 ng/ml, and 0.3 ng/ml).

The measurement method is the same as in Example 11.

Example 13

The Formulation of Human NGF Formulation

1) The Freeze-Dry Formulation of Human NGF:

The content of semi-manufactured NGF was measured by Lowry. The protein solution was diluted with pyrogen-free 25 mM, pH6.8 PB (containing 0.05% human blood albumin and 5% Mannitol) to the volume needed. The solution was filtered with 0.22 μm filter and was aliquoted sterilely. Then the aliquots were frozen, dried, capped and stored at 4° C.

2) The Aqueous Injection of Human NGF

The content of semi-manufactured NGF was measured by Lowry. The protein solution was diluted with pyrogen-free 25 mM, pH6.8 PB (containing 0.05% human blood albumin) to the volume needed. The solution was filtered with 0.22 μm filter and was aliquoted sterilely. Then the aliquots were capped and stored at −20° C.

3) The NGF Eye Drops

The content of semi-manufactured NGF was measured by Lowry. The protein solution was diluted with pyrogen-free 20 mM, pH6.8 PB (containing Glycine, Alanine, Arginine, 3.33 mg/ml (final concentration) respectively, and 0.5% NaCl) to the volume needed. The solution was filtered with 0.22 μm filter and was aliquoted sterilely. Then the aliquots were capped and stored at −20° C.

Example 14

The Formulation of Mutant NGF

The methods are the same as example 13.

Based on the above discussion, many modifications may be made to the present invention. Thus, there are other approaches to perform the present invention, besides the methods discussed above, within the scope of the following appended claims.

The invention claimed is:

1. A transgenic mouse, wherein a polynucleotide sequence encoding a NGF-β protein in the genome of said mouse is replaced with a polynucleotide sequence encoding a human NGF-β protein by homologous recombination, wherein said polynucleotide sequence encoding a human NGF-β protein is the nucleotide sequence of SEQ ID NO: 23, and wherein said mouse expresses said human NGF-β protein.

2. The transgenic mouse of claim 1, wherein said polynucleotide sequence encoding a human NGF-β protein is present in at least one chromosome of said genome of said mouse.

3. The transgenic mouse of claim 1, wherein all NGF-β genes in said genome of said mouse comprise said polynucleotide sequence encoding a human NGF-β protein.

4. A method for obtaining the transgenic mouse of claim 1, said method comprising substituting the coding sequence of the endogenous NGF-β gene of a mouse by homologous recombination with a polynucleotide sequence encoding a human NGF-β protein wherein said method comprises the steps of:

1) constructing a targeting vector, wherein said vector comprises a polynucleotide sequence encoding a human NGF-β protein, wherein said polynucleotide sequence encoding a human NGF-β protein is the nucleotide sequence of SEQ ID NO:23;
2) using the targeting vector obtained in step 1) to transfect mouse embryonic stem cells;
3) preparing a donor mouse blastocyst;
4) microinjecting the transfected embryonic stem cells obtained in step 2) into the donor blastocyst obtained in step 3);
5) transferring the donor blastocyst obtained in step 4) to the uterus of an acceptor mouse; and
6) obtaining the transgenic mouse.

5. A method of preparing a human NGF-β protein, comprising the steps of:

1) feeding the transgenic mouse of claim 1, wherein said mouse expresses said human NGF-β protein, and
2) extracting said human NGF-β protein from the submandibular glands of said mouse.

* * * * *